(12) United States Patent
Kapur et al.

(10) Patent No.: US 6,890,919 B2
(45) Date of Patent: May 10, 2005

(54) ATYPICAL ANTIPSYCHOTIC AGENTS HAVING LOW AFFINITY FOR THE D2 RECEPTOR

(76) Inventors: Shitij Kapur, 334 Carlton Street, Toronto, Ontario (CA), M5A 2M1; Robert McClelland, 8 Wetherfield Place, Toronto, Ontario (CA), M3B 2E1

( * ) Notice: Subject to any disclaimer, the term of this patent is extended or adjusted under 35 U.S.C. 154(b) by 0 days.

(21) Appl. No.: 10/178,618

(22) Filed: Jun. 25, 2002

(65) Prior Publication Data
US 2003/0135042 A1 Jul. 17, 2003

Related U.S. Application Data
(60) Provisional application No. 60/300,430, filed on Jun. 26, 2001.

(51) Int. Cl.[7] .................... C07D 413/04; C07D 417/04; A61K 31/496; A61P 25/18
(52) U.S. Cl. .................. 514/211.13; 540/551
(58) Field of Search ...................... 540/551; 514/211.13

(56) References Cited

U.S. PATENT DOCUMENTS

| | | |
|---|---|---|
| 3,347,849 A | 10/1967 | Schmutz et al. |
| 3,367,930 A | 2/1968 | Schmutz et al. |
| 3,412,193 A | 11/1968 | Coppola |
| 3,444,169 A | 5/1969 | Howell et al. |
| 3,539,573 A | 11/1970 | Schmartz et al. ........... 260/268 |
| 3,546,226 A | 12/1970 | Schmartz et al. ........... 260/268 |
| 3,663,696 A | 5/1972 | Howell et al. |
| 3,681,357 A | 8/1972 | Howell et al. |
| 5,068,437 A | 11/1991 | Kazan et al. |
| 5,393,752 A | 2/1995 | Liegeois et al. |
| 5,538,965 A | 7/1996 | Tehim et al. |
| 5,576,314 A | 11/1996 | Power et al. |
| 5,602,120 A | 2/1997 | Fu et al. |
| 5,602,121 A | 2/1997 | Fu |
| 5,700,445 A | 12/1997 | Fu et al. |
| 5,703,072 A | 12/1997 | Power et al. |
| 5,798,350 A | 8/1998 | Tehim et al. |
| 5,814,628 A | 9/1998 | Fu et al. |
| 5,834,459 A | 11/1998 | Fu ............................. 514/211 |
| 5,968,478 A | 10/1999 | Fu et al. |
| 5,976,497 A | 11/1999 | Pollak et al. |
| 5,998,414 A | 12/1999 | Wang et al. |
| 6,103,715 A | 8/2000 | Tehim et al. |

FOREIGN PATENT DOCUMENTS

| | | |
|---|---|---|
| CH | 422 793 | 4/1967 |
| CH | 436297 | 11/1967 |
| CH | 450 426 | 4/1968 |
| GB | 1164360 | 9/1969 |
| WO | WO 95/17400 | 6/1995 |
| WO | WO 96/18621 | 6/1996 |
| WO | WO 96/18622 | 6/1996 |
| WO | WO 96/18623 | 6/1996 |
| WO | WO 96/18630 | 6/1996 |
| WO | WO 98/01164 | 1/1998 |
| WO | WO 98/07711 | 2/1998 |
| WO | WO 98/37064 | 8/1998 |
| WO | WO 99/00386 | 1/1999 |
| WO | WO 99/31267 | 6/1999 |

OTHER PUBLICATIONS

Edward J. Warawa et al., "Behavioral Approach to Nondyskinetic Dopamine Antagonists: Identification of Seroquel," J. Med. Chem. vol. 44, Feb. 1, 2001, pp. 372–289.

Ahlenius, S., et al., Involvement of Extrapyramidal Motor Mechanisms in the Suppression of Locomotor Activity by Antipsychotic Drugs: A Comparison Between the Effects Produced by Pre– and Post–Synaptic Inhibition by Dopaminergic Neurotransmission, Pharmac., Biochem. & Behavior, vol. 24, pp. 1409–1415 (986).

Bartl, V., et al., Neurotropic and Psychotropic Agents. LXV: 8–Chloro and 8–Isopropyl–6–Piperazinobenzo(b)Pyrido[3, 2–f], Thiepin, Collection Czech. Community (vol. 38), pp. 2778–2787 (1973).

Bartl, V., et al., Neurotropic and Psychotropic Agents. LXI: Derivatives of 6–Piperazinobenzo[b]Pyrido[3,2–f]Thiepin, Collection Czech. Chem. Community (vol. 38), pp. 1693–1699 (1973).

Casey, D.E., Extrapyramidal Syndromes, CMS Drugs, 5 Supp., pp. 1–12 (1996).

Farde, L., et al., Position Emission Tomographic Analysis of Central D1 and D2 Dopamine Receptor Occupancy in Patients Treated With Classical Neuroleptics and Clozapine, Arch. Gen. Psychiatry, vol. 49, pp. 538–544 (1992).

Farde, L., et al., Central D2–Dopamine Receptor Occupancy in Schizophrenic Patients Treated with Antipsychotic Drugs, Arch. Gen. Psychiatry, vol. 45, pp. 71–76 (1988).

(Continued)

*Primary Examiner*—Bruck Kifle
(74) *Attorney, Agent, or Firm*—Harness, Dickey & Pierce, P.L.C.

(57) ABSTRACT

The present invention provides novel compounds of Formula I:

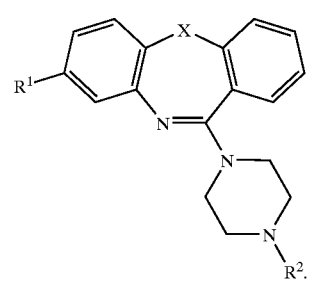

The invention further relates to pharmaceutical compositions comprising compounds of Formula I and to methods of using compounds of Formula I to treat neuropsychiatric disorders (e.g., psychosis, depression, schizophrenia).

10 Claims, No Drawings

OTHER PUBLICATIONS

Jegouzo, A., et al., Comparative oxidation of toxapine and clozapine by human neutrophils, Fundam. Clin. Pharmacol. vol. 13, pp. 113–119 (1999).

Jiler, J., et al., Neurotrope Und Psychotrope Substanzen. XIX: 8–Halogenderivate von 10–(4–Methylpiperzino)–10, 11–Dihydrodibenzo(b,f)Thiepin und Verwandte Substanzen, Collection Czech. Chem. Community (vol. 33), pp. 1831–1845 (1968).

Kapur, S., et al., Does Fast Dissociation From the Dopamine D2 Receptor Explain the Action of Atypical Antipsychotics?: A New Hypothesis, Am. J. Psychiatry, vol. 158:3, pp. 360–369 (Mar. 2001).

Kapur, S., et al., Antipsychotic agents differ in how fast they come of the dopamine D2 receptors. Implications for atypical antipsychotic action, J. Psych. & Neuroscience, vol. 25, No. 2, pp. 161–166 (2000).

Kapur, S., et al., Are Animal Studies of Antipsychotics Appropriately Dosed?: Lessons From the Bedside to the Bench, Can. J. Psychiatry, vol. 45, pp. 241–245 (2000).

Liegeois, J.F., et al., Pyrodibenzoxazepine and Pyridobenzothiazepine Derivatives as Potential Central Nervous System Agents: Synthesis and Neurochemical Study, J. Med. Chem. vol. 37, pp. 519–525, 1994.

Moore, K., Interactions between Prolactin and Dopaminergic Neurons, Biology of Reproduction, vol. 36, pp. 47–58 (1987).

Petz, K., et al., Neurotrope and Psychotrope Substanzen. XXV: Uber dle in 8–Stellung Durch die Methyl–, Tert–Butyl–, Methoxy–, Methylthio–, und methansuffonylgruppe Substituterian 10–(4–Methylpiparazino)–10,11–Dihydrodibenzo(b,f)Thiepin–Derivate, Collection Czach. Chem. Community (vol. 33), pp. 1895–1910 (1968).

Robertson, G. et al., Induction Patterns of Fos–Like Immunoreactivity in the Forebrain as Predictors of Alypical Antipsychotic Activity, Jnl. Pharmacol. & Exper. Therap. vol. 271, No. 2, pp. 1056–1066, 1994.

Seeman, P. et al., Deriving the therapeutic concentrations for clozapine and hatoperidol: The apparent dissociation constant of a neuroleptic at the dopamine $D_2$ receptor varies with the affinity of the competing radioligand, Eur. Jnl of Pharmac., Molecular Pharmac. Section 291, pp. 59–68, (1993).

Seeman, P. et al., Antipsychotic drugs with alicit little or no Parkinsonism bind more loosely than dopamine to brain D2 receptors, yet occupy high levels of these receptors, Molecular Psych. vol. 3, pp. 123–134, (1998).

Seeman, P. et al., Rapid release of Antipsychotic Drugs From Dopamine $D_2$ Receptors: An Explanation for Low Receptor Occupancy and Early Clinical Relapse Upon Withdrawl fo Ciozapine or Quetispine. Am. J. Psychiatry.

Uetrcht, J. et al., Structural features associated with reactive metabolite formation in clozapine analogues, Chemico–Biological Interactions, vol. 104, pp. 117–129 (1997).

Uetrecht, J. et al., Reactive metabolites and agranulocytosis, Eur. Jnl Haemotology, vol. 57, pp. 83–88 (1998).

Wadenberg, M. et al., Dopamine $D_2$ receptor occupancy predicts catalepsy and the suppression of conditioned avoidance response behavior in rats, Psychopharmacology, vol. 150, pp. 420–429 (2000).

Hans O. Kalkman et al., The role of $D_2$–adrenoceptor antagonism in the anti–cataleptic properties of the atypical neuroleptic agent, clozapine, in the rat, British J. of Phamacology, 124:1550–1558 (1998).

K. H. McAllister et al., "Clozapine reversal of the deficits in coordinated movement induced by D2 receptor blockade does not depend upon antagonism of $\alpha 2$ andrenoceptors," Naunym–Schmiedeberg's Arch. Pharmacol. 360:603–608 (1999).

Philip Seemane et al., "Role of dopamine D2, D4 and serotonin2A receptors in antipsychotic and anticataleptic action," J. Psychophamacology, 11(1), pp. 15–17 (1997).

ATYPICAL ANTIPSYCHOTIC AGENTS HAVING LOW AFFINITY FOR THE D2 RECEPTOR

CROSS-REFERENCE TO RELATED APPLICATION

This application claims priority to U.S. Provisional Patent Application Ser. No. 60/300,430, filed Jun. 26, 2001, which is hereby incorporated by reference in its entirety.

FIELD OF THE INVENTION

This invention relates to novel compounds and their use as antipsychotics. In particular, the invention relates to compounds having a typical dopamine receptor affinity, methods of preparing such compounds and to their use for therapeutic and drug screening purposes.

BACKGROUND OF THE INVENTION

There are currently several antipsychotics available for regular clinical use. Every one of them blocks dopamine $D_2$ receptors (Seeman and Tallerico 1998). See Index of Articles cited herein. This includes the older "typical" as well as the newer "atypical" antipsychotics. "Atypical" antipsychotic is a term that is used to define antipsychotics which have a lower or minimal incidence of side effects. With the exception of a few dopamine-depleting agents, there is no receptor-drug profile other than $D_2$ receptor blockage that is able to achieve antipsychotic activity. However, a central problem in the use of antipsychotics is that of related side effects. The two major side effects of concern have been extrapyramidal side effects ("EPS") as well as prolactin elevation. Side effects limit the number of patients who agree to take these medications, as they tend to decrease compliance and high levels of EPS may actually decrease the efficacy of the medications.

Without being bound by theory, it is believed that EPS and prolactin elevation also result from dopamine $D_2$ blockade. In particular, the blockade of $D_2$ receptors in the tuberoinfundibular system is thought to be responsible for prolactin elevation (Moore 1987), while the blockade of the dopamine $D_2$ receptors in the striatum is thought to be responsible for EPS (Farde et al. 1997). A corollary of prolonged blockade of the dopamine $D_2$ system is thought to be tardive dyskinesia which occurs after several years of use of antipsychotics that cause EPS (Casey 1996). Thus, avoiding these side effects is a central way of improving antipsychotics.

The current gold-standard for an a typical antipsychotic is clozapine. However, in some patients clozapine has the serious shortcoming of blood dyscrasias, or agranulocytosis, which means that all patients on this medication must have their blood tested regularly. This side-effect is the Achille's heel of clozapine. It has limited the use of this most effective antipsychotic (in terms of efficacy and "atypicality") to being the drug of last resort because of this ongoing need for regular blood testing of each patient on the medication.

There is therefore a need for new effective antipsychotic drugs exhibiting minimal side effects (e.g., diminished or absent EPS, prolactin elevation and/or agranulocytosis side effects).

SUMMARY OF THE INVENTION

Novel tricyclic piperazine compounds have been prepared and found to have a high $K_i$ (Note: $K_i = K_{off}/K_{on}$) for the dopamime $D_2$ receptor of at least 30 nM, preferably above about 40 nM, and/or a $K_{off}$ sufficiently large to enable interaction between the dopamine $D_2$ receptor and the novel compound(s) to yield their beneficial "atypical" antipsychotic efficacy i.e., with greatly diminished or without the side effects associated with the "typical" antipsychotics. These compounds have been shown to act as a typical antipsychotics in animal behavior assays.

The present invention therefore provides compounds of Formula I:

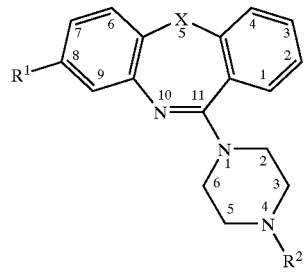

wherein:

$R^1$ is selected from the group consisting of halo, $CF_3$, $CF_3O$, cyano, $CH_3$ and $CH_3O$;

$R^2$ is selected from the group consisting of $C_{2-5}$alkyl and $(CH_2)_nOH$;

X is selected from the group consisting of O and S;

n is 2–5; and pharmaceutically acceptable salts, hydrates, prodrugs and solvates thereof.

According to other embodiments of the present invention, the above compounds of Formula I have a $K_i$ value (affinity for the dopamine $D_2$ receptor) as noted below in items (1) to (12). Also, the below-noted $K_i$ values are measured according to the procedures described in Seeman 1993 (cited herein) using raclopride as the standard ligand:

(1) $K_i$ value for the dopamine $D_2$ receptor of at least 30 nM (nanomoles);

(2) $K_i$ value for the dopamine $D_2$ receptor from 30 nM to about 500 nM;

(3) $K_i$ value for the dopamine $D_2$ receptor of at least about 40 nM;

(4) $K_i$ value for the dopamine $D_2$ receptor from about 40 nM to about 50 nM;

(5) $K_i$ value for the dopamine $D_2$ receptor from about 40 nM to about 250 nM;

(6) $K_i$ value for the dopamine $D_2$ receptor from about 40 nM to about 180 nM;

(7) $K_i$ value for the dopamine $D_2$ receptor from about 40 nM to about 120 nM;

(8) $K_i$ value for the dopamine $D_2$ receptor from about 40 nM to about 80 nM;

(9) $K_i$ value for the dopamine $D_2$ receptor of at least about ½×($K_i$ for clozapine);

(10) $K_i$ value for the dopamine $D_2$ receptor from about ½×($K_i$ for clozapine) to about ½×($K_i$ for clozapine);

(11) $K_i$ value for the dopamine $D_2$ receptor from about ½×($K_i$ for clozapine) to about 4×($K_i$ for clozapine); and

(12) $K_i$ value for the dopamine $D_2$ receptor from about ½×($K_i$ for clozapine) to about 2×($K_i$ for clozapine).

The present invention also provides compounds of Formula I wherein $R^1$ is selected from the group consisting of halo and $CF_3$ and wherein $R^2$, X and n are as defined in Formula I.

The present invention also provides compounds of Formula I wherein $R^1$ is selected from the group consisting of F, Cl and $CF_3$, and wherein $R^2$, X and n are as defined in Formula I.

Further, the present invention provides compounds of Formula I wherein $R^1$ is Cl and wherein $R^2$, X and n are as defined in Formula I.

There are also provided compounds of Formula I wherein $R^1$ is selected from the group consisting of $C_{2-4}$ alkyl and $(CH_2)_nOH$ and wherein $R^1$, X and n are as defined in Formula I. Further, the present invention provides compounds of Formula I wherein $R^2$ is selected from the group consisting of ethyl, n-propyl, isopropyl, butyl and $(CH_2)_2OH$ and wherein $R^1$ and X are as defined in Formula I. The present invention further provides compounds of Formula I wherein $R^2$ is selected from the group consisting of ethyl and $(CH_2)_2OH$ and wherein $R^1$ and X are as defined in Formula I.

There are also provided compounds of Formula I wherein X is O and wherein $R^2$, $R^1$ and n are as defined in Formula I.

The invention further relates to pharmaceutical compositions comprising a compound of Formula I and a pharmaceutically acceptable carrier and/or diluent.

According to another broad aspect of the present invention, there is provided a method of treating neuropsychiatric disorders (including, but not limited to, conditions associated with or leading to psychosis, emotional and behavioral disturbances, schizophrenia and schizophrenia spectrum disorders, psychotic disorders in the context of affective disorders, depression, psychosis disorders induced by drugs/medication (such as Parkinson's psychosis), drug induced movement disorders (dyskinesias in Parkinson's disease), psychosis and behavioral disorders in the context of dementias and psychotic disorders due to a general medical conditions, or combinations thereof) comprising administering to a patient or subject (e.g., a human or an animal such as a dog) in need thereof a therapeutically effectively amount of a compound of Formula I. Preferably, the compound of Formula I is combined with a pharmaceutically acceptable carrier and/or diluent.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

1. Definitions

The term "halo" as used herein means halogen and includes chloro, fluoro, bromo, and iodo.

The term "$C_{2-5}$alkyl" as used herein means straight and branched chain alkyl radicals containing from two to five carbon atoms and includes ethyl, propyl, isopropyl, n-butyl, t-butyl, n-pentyl and the like.

The term "compound(s) of the invention" as used herein means a compound of Formula I and salts, hydrates, prodrugs and solvates thereof.

The term "pharmaceutically acceptable salt" means an acid addition salt which is suitable for or compatible with the treatment of a patient or a subject such as a human patient or an animal such as a dog.

The term "pharmaceutically acceptable acid addition salt" as used herein means any non-toxic organic or inorganic salt of any base compounds represented by Formula I or any of their intermediates. Illustrative inorganic acids which form suitable acid addition salts include hydrochloric, hydrobromic, sulfuric and phosphoric acids, as well as metal salts such as sodium monohydrogen orthophosphate and potassium hydrogen sulfate. Illustrative organic acids that form suitable acid addition salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g. oxalates, may be used, for example, in the isolation of compounds of Formula I for laboratory use, or for subsequent conversion to a pharmaceutically acceptable acid addition salt.

The term "solvate" as used herein means a compound of Formula I, or a pharmaceutically acceptable salt of a compound of Formula I, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate."

The term an "effective amount" or a "sufficient amount" of an agent as used herein is that amount sufficient to effect beneficial or desired results, including clinical results, and, as such, an "effective amount" depends upon the context in which it is being applied. For example, in the context of administering an agent that acts as an a typical antipsychotic, an effective amount of an agent is, for example, an amount sufficient to achieve such a reduction in psychoses, without unwanted side effects such as, for example EPS and prolactin elevation, as compared to the response obtained without administration of the agent. The term "effective amount" also includes that amount of the compound of Formula I which is "therapeutically effective" and which avoids or substantially attenuates undesirable side effects such as EPS, prolactin elevation and/or blood dyscrasias.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

To "diminish" or "inhibit" or "suppress" or "reduce" a function or activity, such as psychoses, is to reduce the function or activity when compared to otherwise same conditions except for a condition or parameter of interest, or alternatively, as compared to another condition.

The terms "animal," "subject" and "patient" as used herein include all members of the animal kingdom including, but not limited to, mammals, animals (e.g. cats, dogs, horses, etc.) and humans. The animal is preferably a human.

As used herein "low binding affinity" means a relatively high $K_i$, of at least 30 nM (or at least about 40 nM), or of at least about ½×($K_i$ for clozapine) sufficient to yield the beneficial antipsychotic effects associated with "atypical" antipsychotics with reduced or diminished or altogether without the detrimental side effects of "typical" antipsychotics such as EPS etc. described above. The "low binding affinity" may be one that falls within ranges of items (1) to (12) noted above measured using raclopride as the standard ligand. As will be appreciated by those skilled in the art, $K_i$ values depend on the method of measurement, pH, radiolabeling technique, tissue type, temperature and type of wash used. The greatest differences depend upon the ligand standard used, for example with clozapine, a $K_i$ of 76 nM is obtained with raclopride as the standard, but a $K_i$ of 180 nM is obtained when spiperone is used as the standard, even under identical conditions. Accordingly, $K_i$ and "low binding affinity" as used herein encompass this understanding and the $K_i$ values recited herein are based on $K_i$ values measured using raclopride as the standard according to the procedure outlined in Seeman 1993. Preferably, a control $K_i$ measurement should be made simultaneously, for example, with clozapine to standardize the $K_i$ value measured to offset any effects of variations in the measuring conditions such as pH, temperature, tissue type etc. noted above.

As used herein a "fast off-rate" means a relatively high $K_{off}$, on the order of approximately 0.6 min$^{-1}$ or greater sufficient to yield the beneficial antipsychotic effects associated with "atypical" antipsychotics with reduced or diminished or altogether without the detrimental side effects of "typical" antipsychotics such as EPS etc. described above. The same consideration in respect of $K_i$ and low binding affinity also apply to $K_{off}$ and "fast off-rate". Thus, the "fast off-rate" may be one that falls within ranges of items (1)–(12) noted above using clozapine as the standard. See Kapur and Seaman 2000a.

2. Preferred Compounds of the Invention

As hereinbefore described, it is expected that a typical antipsychotic activity may be achieved with a drug that blocks the dopamine $D_2$ receptor with a high $K_i$, preferably of at least 30 nM, and/or a fast off-rate ($K_{off}$), preferably greater than about 0.6 min$^{-1}$ sufficient to yield the beneficial antipsychotic effects associated with "atypical" antipsychotics with reduced or diminished or altogether without the detrimental side effects of "typical" antipsychotics such as EPS etc. described above. Exemplary $K_{off}$ values suitable for use with the present invention include, but are not limited to, from about 0.6 min$^{-1}$ to about 10.0 min$^{-1}$, from about 0.8 min$^{-1}$ to about 10.0 min$^{-1}$, from about 0.9 min$^{-1}$ to about 9.0 min$^{-1}$, from about 1.0 min$^{-1}$ to about 8.0 min$^{-1}$, from about 1.1 min$^{-1}$ to about 7.0 min$^{-1}$, from about 1.2 min$^{-1}$ to about 6.0 min$^{-1}$, from about 1.5 min$^{-1}$ to about 5.0 min$^{-1}$, and from about 1.8 min$^{-1}$ to about 3.2 min$^{-1}$. The measurement for $K_{off}$ may be made according to the procedure outlined in Kapur and Seaman 2000a.

As noted above, according to one embodiment, the invention relates to novel compounds that have a $K_i$ for the $D_2$ receptor of at least 30 nM and/or a $K_{off}$ greater than about 0.6 min$^{-1}$. It has been found, more particularly, that $D_2$-binding ligands having the tricyclic structure:

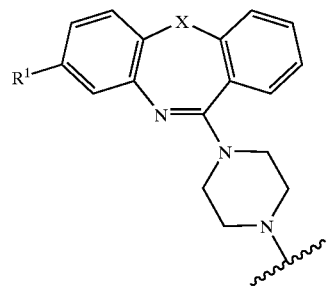

have a $K_i$ of at least 30 nM and/or a $K_{off}$ of at least about 0.6 min$^{-1}$ (sufficient to yield the beneficial antipsychotic effects associated with "atypical" antipsychotics with reduced or diminished or altogether without the detrimental side effects of "typical" antipsychotics such as EPS etc. described above), and therefore are effective as atypical antipsychotics, when the piperazine group is derivatized by a group designated $R^2$ as noted below. In accordance with one of its aspects, the present invention therefore provides compounds of Formula I:

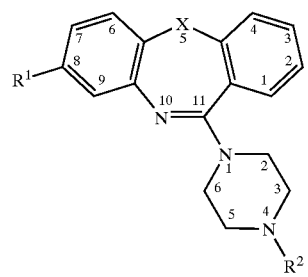

I wherein $R^1$ is selected from the group consisting of halo, $CF_3$, $CF_3O$, cyano, $CH_3$ and $CH_3O$;

$R^2$ is selected from the group consisting of $C_{2-5}$alkyl and $(CH_2)_nOH$;

X is selected from the group consisting of O and S;

n is 2–5; and pharmaceutically acceptable salts, hydrates, prodrugs and solvates thereof.

In accordance with one of its embodiments, the present invention therefore provides compounds of Formula I:

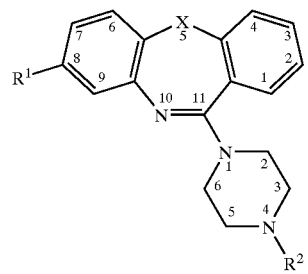

I wherein:

$R^1$ is selected from the group consisting of halo, $CF_3$, $CF_3O$, cyano, $CH_3$ and $CH_3O$;

$R^1$ is selected from the group consisting of $C_{2-5}$alkyl and $(CH_2)_nOH$;

X is selected from the group consisting of O and S;
n is 2–5; and
a pharmaceutically acceptable salt, hydrate, prodrug or solvate thereof; and wherein:
said compound of Formula I has a $K_i$ for the dopamine $D_2$ receptor in any one of the value ranges noted in items (1) to (12) as follows:

(1) $K_i$ value for the dopamine $D_2$ receptor of at least 30 nM (nanomoles);
(2) $K_i$ value for the dopamine $D_2$ receptor from 30 nM to about 500 nM;
(3) $K_i$ value for the dopamine $D_2$ receptor of at least about 40 nM;
(4) $K_i$ value or the dopamine $D_2$ receptor from about 40 nM to about 500 nM;
(5) $K_i$ value for the dopamine $D_2$ receptor from about 40 nM to about 250 nM;
(6) $K_i$ value for the dopamine $D_2$ receptor from about 40 nM to about 180 nM;
(7) $K_i$ value for the dopamine $D_2$ receptor from about 40 nM to about 120 nM;
(8) $K_i$ value for the dopamine $D_2$ receptor from about 40 nM to about 80 nM;
(9) $K_i$ value for the dopamine $D_2$ receptor of at least about ½×($K_i$ for clozapine);
(10) $K_i$ value for the dopamine $D_2$ receptor from about ½×($K_i$ for clozapine) to about 6½×($K_i$ for clozapine);
(11) $K_i$ value for the dopamine $D_2$ receptor from about ½×($K_i$ for clozapine) to about 4×($K_i$ for clozapine); and
(12) $K_i$ value for the dopamine $D_2$ receptor from about ½×($K_i$ for clozapine) to about 2×($K_i$ for clozapine).

As previously noted, the above-noted $K_i$ values are measured according to the procedure described in Seeman 1993 (cited herein) using raclopride as the standard ligand.

In embodiments of the invention, compounds of Formula I are those in which $R^1$ is selected from the group consisting of halo, $CF_3$, $CF_3O$, cyano, $CH_3$ and $CH_3O$. Preferably, $R^1$ is selected from the group consisting of halo and $CF_3$. In more preferred embodiments, $R^1$ is selected from the group consisting of F, Cl and $CF_3$. In the most preferred embodiment, $R^1$ is Cl.

Further embodiments of the invention include compounds of Formula I wherein $R^1$ is selected from the group consisting of $C_{2-5}$alkyl and $(CH_2)_n$OH, where n is 2, 3, 4 or 5. Preferred embodiments include compounds of Formula I where $R^2$ is selected from the group consisting of $C_{2-4}$ alkyl and $(CH_2)_n$OH and n is 2–3. More preferably, $R^2$ is selected from the group consisting of ethyl, n-propyl, isopropyl, butyl and $(CH_2)_2$OH. Most preferred are compounds of Formula I wherein $R^2$ is selected from the group consisting of ethyl and $(CH_2)_2$OH.

Compounds of Formula I further include those in which X is selected from O and S. The oxazepines and thiazepines are expected to have a reduced propensity for the hematological side-effect, agranulocytosis (Uetrecht et al. 1997). This particular side effect is responsible for the limited clinical use of clozapine. Preferred are compounds of Formula I where X is O.

In specific embodiments of the invention, the compounds of Formula I include:

(A-1) 8-Trifluoromethyl-11-(4-ethylpiperazin-1-yl)-dibenzo[b,f][1,4]oxazepine;
(A-2) 8-Trifluoromethyl-11-(4-(2'-hydroxyethyl)piperazin-1-yl)-dibenzo[b,f][1,4]oxazepine;
(A-3) 8-Trifluoromethyl-11-(4-propylpiperazin-1-yl)-dibenzo[b,f][1,4]oxazepine;
(A-3a) 8-Trifluoromethyl-11-(4-propylpiperazin-1-yl)-dibenzo[b,f][1,4]oxazepine.HCl;
(A-4) 8-Trifluoromethyl-11-(4-isopropylpiperazin-1-yl)-dibenzo[b,f][1,4]oxazepine;
(A-4a) 8-Trifluoromethyl-11-(4-isopropylpiperazin-1-yl)-dibenzo[b,f][1,4]oxazepine.HCl;
(A-5) 8-Trifluoromethyl-11-(4-butylpiperazin-1-yl)-dibenzo[b,f][1,4]oxazepine;
(A-5a) 8-Trifluoromethyl-11-(4-butylpiperazin-1-yl)-dibenzo[b,f][1,4]oxazepine.HCl;
(A-6) 8-Chloro-11-(4-ethylpiperazin-1-yl)-dibenzo[b,f][1,4]oxazepine;
(A-6a) 8-Chloro-11-(4-ethylpiperazin-1-yl)-dibenzo[b,f][1,4]oxazepine.HCl;
(A-7) 8-Chloro-11-(4-(2'-hydroxyethyl)piperazin-1-yl)-dibenzo[b,f][1,4]oxazepine;
(A-8) 8-Chloro-11-(4-propylpiperazin-1-yl)-dibenzo[b,f][1,4]oxazepine;
(A-9) 8-Chloro-11-(4-isopropylpiperazin-1-yl)-dibenzo[b,f][1,4]oxazepine;
(A-10) 8-Chloro-11-(4-butylpiperazin-1-yl)-dibenzo[b,f][1,4]oxazepine;
(A-11) 8-Fluoro-11-(4-ethylpiperazin-1-yl)-dibenzo[b,f][1,4]oxazepine;
(A-12) 8-Chloro-11-(4-ethylpiperazin-1-yl)-dibenzo[b,f][1,4]thiazepine;
(A-13) 8-Chloro-11-(4-(2'-hydroxyethyl)piperazin-1-yl)-dibenzo[b,f][1,4]thiazepine;
(A-14) 8-Chloro-11-(4-propylpiperazin-1-yl)-dibenzo[b,f][1,4]thiazepine;
(A-14a) 8-Chloro-11-(4-propylpiperazin-1-yl)-dibenzo[b,f][1,4]thiazepine.HCl;
(A-15) 8-Chloro-11-(4-isopropylpiperazin-1-yl)-dibenzo[b,f][1,4]thiazepine;
(A-15a) 8-Chloro-11-(4-isopropylpiperazin-1-yl)-dibenzo[b,f][1,4]thiazepine.HCl;
(A-16) 8-Chloro-11-(4-butylpiperazin-1-yl)-dibenzo[b,f][1,4]thiazepine; and
(A-16a) 8-Chloro-11-(4-butylpiperazin-1-yl)-dibenzo[b,f][1,4]thiazepine.HCl.

More specifically the compounds of Formula I include:

(A-1) 8-Trifluoromethyl-11-(4-ethylpiperazin-1-yl)-dibenzo[b,f][1,4]oxazepine;
(A-2) 8-Trifluoromethyl-11-(4-(2'-hydroxyethyl)piperazin-1-yl)-dibenzo[b,f][1,4]oxazepine;
(A-6) 8-Chloro-11-(4-ethylpiperazin-1-yl)-dibenzo[b,f][1,4]oxazepine;
(A-6a) 8-Chloro-11-(4-ethylpiperazin-1-yl)-dibenzo[b,f][1,4]oxazepine.HCl;
(A-7) 8-Chloro-11-(4-(2'-hydroxyethyl)piperazin-1-yl)-dibenzo[b,f][1,4]oxazepine;
(A-11) 8-Fluoro-11-(4-ethylpiperazin-1-yl)-dibenzo[b,f][1,4]oxazepine;
(A-12) 8-Chloro-11-(4-ethylpiperazin-1-yl)-dibenzo[b,f][1,4]thiazepine; and
(A-13) 8-Chloro-11-(4-(2'-hydroxyethyl)piperazin-1-yl)-dibenzo[b,f][1,4]thiazepine.

Even more specifically, the compounds of Formula I include:

(A-6) 8-Chloro-11-(4-ethylpiperazin-1-yl)-dibenzo[b,f][1,4]oxazepine;

(A-6a) 8-Chloro-11-(4-ethylpiperazin-1-yl)-dibenzo[b,f][1,4]oxazepine.HCl;
(A-7) 8-Chloro-11-(4-(2'-hydroxyethyl)piperazin-1-yl)-dibenzo[b,f][1,4]oxazepine;
(A-12) 8-Chloro-11-(4-ethylpiperazin-1-yl)-dibenzo[b,f][1,4]thiazepine; and
(A-13) 8-Chloro-11-(4-(2'-hydroxyethyl)piperazin-1-yl)-dibenzo[b,f][1,4]thiazepine.

Most specifically, the compounds of Formula I include:

(A-6) 8-Chloro-11-(4-ethylpiperazin-1-yl)-dibenzo[b,f][1,4]oxazepine;
(A-6a) 8-Chloro-11-(4-ethylpiperazin-1-yl)-dibenzo[b,f][1,4]oxazepine.HCl; and
(A-7) 8-Chloro-11-(4-(2'-hydroxyethyl)piperazin-1-yl)-dibenzo[b,f][1,4]oxazepine.

3. Methods of Preparing Compounds of Formula I

Compounds of Formula I may be prepared using processes analogous to those known in the art. The present invention therefore provides, in a further aspect, a process for the preparation of a compound of Formula I, or a salt, solvate or hydrate thereof, which comprises the step of coupling a reagent of Formula A with a reagent of Formula B, as shown in Scheme 1, wherein $R^1$ and $R^2$ and X are as defined in Formula 1. Reagents of Formula A may be prepared from the corresponding lactams 2 by, for example, reaction with phosphorus oxychloride in an inert solvent, such as toluene, in the presence of an organic base, such as a tertiary amine, preferably at refluxing temperatures. Reagents A need not be isolated, but instead may be reacted directly with reagents of Formula B in an inert solvent such as toluene, preferably at refluxing temperatures. Alternatively, Reagents of Formula 2 may be reacted with a reagent of Formula B in the presence of a Lewis Acid such as $TiCl_4$ or $BF_3Et_2O$ to provide compounds of Formula I.

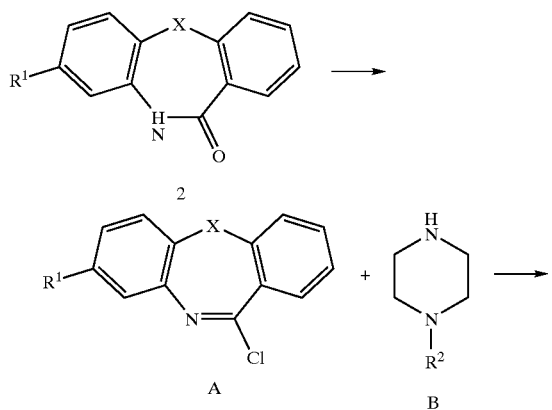

Scheme 1

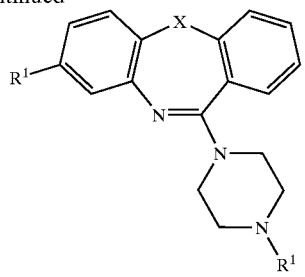

I

Lactams 2, where X=O, may be prepared according to the procedures described in Klunder (J. Med. Chem. 1992, 35:1887). Alternatively, lactams 2, where X is O or S, may be prepared as shown in Scheme 2. Appropriately 4-substituted nitrobenzenes 3, wherein Y is a suitable leaving group such as halo, preferably fluoro or chloro, may be condensed with either aldehyde or esters 4, wherein X is O or S, using, for example potassium fluoride on alumina and phase transfer catalysis or by treating reagents 4 with a strong base, such as sodium hydride or sodium hydroxide, followed by the addition of reagents 3. Reduction of the nitro group, for example by Raney nickel catalyzed reduction, followed by saponification of the ester or oxidation of the aldehyde gives, after acidification (if necessary), an intermediate amino acid 5 that may be cyclized to lactam 2 by refluxing in an inert solvent such as xylenes or hexanes.

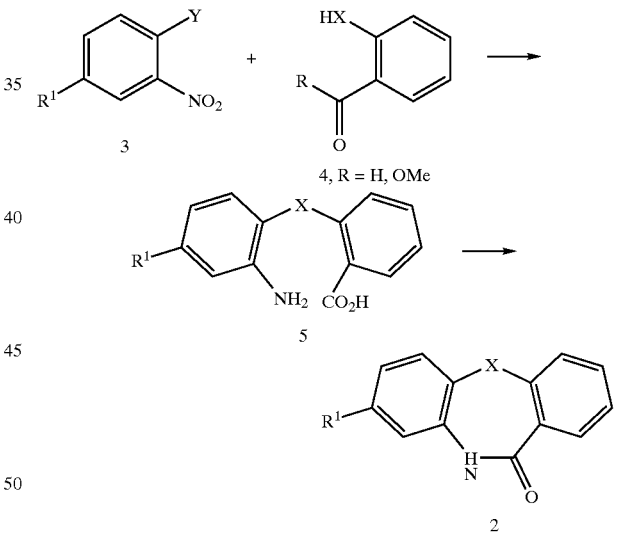

Reagents of Formula B are either commercially available or may be prepared using known procedures. For example, suitably mono-protected piperazines may be reacted with a compound of the formula Y—$C_{2-5}$alkyl or Y—$(CH_2)_n$OP, where Y is a leaving group such as halo and P is a suitable protecting group, in the presence of a base in an inert solvent, followed by removal of the protecting groups.

In some cases the chemistries outlined above may have to be modified, for instance by use of protective groups, to prevent side reactions due to reactive groups, such as reactive groups attached as substituents. This may be achieved by means of conventional protecting groups, for example as described in "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, 1991.

The formation of a desired compound salt is achieved using standard techniques. For example, the neutral compound is treated with an acid in a suitable solvent and the formed salt is isolated by filtration, extraction or any other suitable method. The conversion of a given compound salt to a desired compound salt is achieved by applying standard techniques, in which an aqueous solution of the given salt is treated with a solution of base, e.g. sodium carbonate or sodium or potassium hydroxide, to liberate the free base which is then extracted into an appropriate solvent, such as ether. The free base is then separated from the aqueous portion, dried and treated with the requisite acid as described above to give the desired salt.

The formation of solvates of the compounds of the invention will vary depending on the compound and the solvate. In general, solvates are formed by dissolving the compound in the appropriate solvent and isolating the solvate by cooling or using an antisolvent. The solvate is typically dried or azeotroped under ambient conditions.

Prodrugs of the compounds of the invention may be conventional esters formed with available hydroxy, amino or carboxyl group. For example, when $R^2$ is $(CH_2)_nOH$ in a compound of Formula I, it may be acylated using an activated acid in the presence of a base, and optionally, in inert solvent (e.g. an acid chloride in pyridine). Some common esters which have been utilized as prodrugs are phenyl esters, aliphatic $(C_8-C_{24})$ esters, acyloxymethyl esters, carbamates and amino acid esters.

A radiolabeled compound of the invention may be prepared using standard methods known in the art. For example, tritium may be incorporated into a compound of the invention using standard techniques, for example by hydrogenation of a suitable precursor to a compound of the invention using tritium gas and a catalyst. Alternatively, a compound of the invention containing radioactive iodo may be prepared from the corresponding trialkyltin (suitably trimethyltin) derivative using standard iodination conditions, such as $[^{125}I]$ sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, for example hexamethylditin in the presence of tetrakis(triphenylphosphine) palladium (0) in an inert solvent, such as dioxane, and at elevated temperatures, suitably 50–100° C.

4. Pharmaceutical Compositions

The compounds of the invention are preferably formulated into pharmaceutical compositions for administration to human subjects in a biologically compatible form suitable for administration in vivo. Accordingly, in another aspect, the present invention provides a pharmaceutical composition comprising a compound of Formula I in admixture with a suitable diluent and/or carrier.

The compositions containing the compounds of the invention can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985 and each of its later editions published to date). On this basis, the compositions include, albeit not exclusively, solutions of the substances in association with one or more pharmaceutically acceptable vehicles and/or diluents, and are contained in buffered solutions with a suitable pH and are iso-osmotic with the physiological fluids.

In accordance with the methods of the invention, the described compounds or salts or solvates thereof may be administered to a patient in a variety of forms depending on the selected route of administration, as will be understood by those skilled in the art. The compositions of the invention may be administered orally or parenterally. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

A compound of the invention or a salt or solvate thereof may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound of the invention may be incorporated with excipient and used in the form of ingestible tablets, buccal tablets, troches, capsules, elixirs, suspensions, syrups, wafers, and the like.

A compound of the invention may also be administered parenterally or intraperitoneally. Solutions of a compound of the invention as a free base or pharmacologically acceptable salt or solvate can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (1990—18th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists.

The compounds of the invention may be administered to an animal alone or in combination with pharmaceutically acceptable carriers and/or diluents, as noted above, the proportion of which is determined by the solubility and chemical nature of the compound, chosen route of administration and standard pharmaceutical practice.

Preferably, the composition is in unit dose form such as a tablet, capsule or ampoule. Suitable unit doses, i.e. therapeutically effective amounts, can be determined during clinical trials designed appropriately for each of the conditions for which administration of a chosen compound is indicated and will of course vary depending on the desired clinical endpoint. It is anticipated that dosage sizes appropriate for administering the compounds of the invention will be roughly equivalent to those used currently for clozapine. Accordingly, each dosage unit for oral administration may contain from about 1 mg to about 500 mg, preferably from about 5 mg to about 450 mg, more preferably from about 10 mg to about 400 mg, even more preferably from about 15 mg to about 350 mg and most preferably from about 20 mg to about 300 mg and will be administered in a frequency appropriate for initial and maintenance treatments. In particular, on a routine basis, compounds of Formula I, will need to be given in a high concentration, the concentration which would bring the occupancy into the same range as other psychotic drugs. However, in the body of the recipient things are dynamic, and in the face of dynamic fluxes of dopamine these drugs with a fast $K_{off}$ lead to a faster approach to equilibrium as well as more competitive displacement by dopamine.

5. Uses

The present invention provides a new range of treatments of patients with psychotic disorders, preferably dopamine-related neuropsychiatric disorders. Accordingly, the present invention provides a method of treating neuropsychiatric disorders (including, but not limited to, conditions associated with or leading to psychosis, emotional and behavioral disturbances, schizophrenia and schizophrenia spectrum disorders, psychotic disorders in the context of affective disorders, depression, psychosis disorders induced by drugs/medication (such as Parkinson's psychosis), drug induced movement disorders (dyskinesias in Parkinson's disease), psychosis and behavioral disorders in the context of dementias and psychotic disorders due to a general medical conditions, or combinations thereof), comprising administering to a subject in need thereof an effective amount of a compound of Formula I. Preferably, the subject is a human or an animal (e.g., a dog) and the compound of Formula I is combined with a pharmaceutically acceptable carrier and/or diluent to provide a dosage composition as described hereinabove.

While not wishing to be bound to any one theory, it is hypothesized that it is the low receptor occupancy of the $D_2$ receptor with a drug having a high $K_i$ and/or fast $K_{off}$, which explain the "atypicality" of the compounds of the present invention. Affinity (more precisely, $K_i$) is, by definition, the ratio of $K_{off}/K_{on}$ (the rate at which the drug moves off of and on to the receptor). In theory, either a difference in $K_{on}$ and/or a difference in $K_{off}$ could lead to low affinity. To examine where $K_{on}$ or $K_{off}$ drives the differences in $D_2$ affinity between typical and a typical antipsychotics, the affinity, $K_{on}$ and $K_{off}$ were measured for a series of typical and atypical antipsychotics (Kapur and Seeman 2000a). Although affinity for the $D_2$ receptor varied nearly a thousand-fold, from 0.025 nM for nemonapride to 155 nm for quetiapine, 99% of the difference in affinity of the antipsychotics was driven by differences in their $K_{off}$ at the $D_2$ receptor. Differences in $K_{on}$ did not account for any significant differences in affinity. All antipsychotics (typical or a typical) attach to the $D_2$ receptor with a similar rate constant; they typically differ only in how fast they come off of the receptor. It is proposed that this relationship between fast $K_{off}$ and low affinity is an important underlying molecular feature that explains why low affinity at the $D_2$ receptor leads to the a typical antipsychotic effect with diminished or without the "typical" antipsychotic side effect profile. This theory also explains why drugs like risperidone and olanzapine do not act as atypical as clozapine (since their $K_{off}$ is not as fast). Furthermore, this hypothesis has the ability to explain one fact that no previous hypothesis can explain, why drugs like remoxipride and amisulpride, which are pure $D_2/D_3$ antagonists demonstrate features of atypical antipsychotics. However, there is a limit to how fast one would want $K_{off}$. Water, theoretically, has one of the fastest $K_{off}$ on the dopamine receptor. While it does not give rise to side-effects, it is also not efficacious. Since some element of $D_2$ occupancy is essential to obtain antipsychotic effect, there is an optimal value of $K_{off}$ which maximizes response with minimal side-effects.

The compounds of Formula I are useful since they demonstrate characteristics of atypical antipsychotic drugs with diminished or without the typical side effect antipsychotic drug profile. The compounds of Formula I are expected to provide improved psychotic symptoms without EPS with secondary improvement in negative symptoms, mood and cognition. While not wishing to limit the full range of disorders in animals which will benefit, compounds of Formula I are expected to be useful in conditions associated with or leading to psychosis and emotional and behavioral disturbances, including but not limited to schizophrenia and schizophrenia spectrum disorders; psychotic disorders in the context of affective disorders such as depression; psychotic disorders induced by drugs/medications (such as Parkinson's psychosis); drug-induced movement disorders (dyskinesias in Parkinson's Disease); psychotic and behavioral disorders in the context of dementias; and psychotic disorders due to a general medical condition.

As herein before mentioned, the side effect of agranulocytosis has limited the use of clozapine, the most effective antipsychotic (in terms of efficacy and "atypicality") to being the drug of last resort. The best of current evidence suggests that clozapine's agranulocytosis is linked to its reactive metabolites (Uetrecht 1996). Furthermore, studies suggest that if one uses the tricyclic structure with an oxygen (dibenzoxazepine) or sulphur bridge (dibenzothiazepine) instead of the nitrogen (dibenzazepines) these reactive metabolites can be avoided (Uetrecht et al. 1997). This is supported by evidence that drugs which are similar to clozapine but avoid the dibenzazepine, e.g. the dibenzoxazepines such as loxapine and amoxapine, have never been implicated in agranulocytosis despite many years of use in high doses (Jegouzo et al. 1999). The compounds of the present invention, being oxazepines and thiazepines, are not expected to have the agranulocytosis side effect.

As hereinbefore mentioned, the inventors have prepared novel compounds of Formula I. Accordingly, the present invention includes all uses of the compounds of the invention including their use in therapeutic methods and compositions as antipsychotics, their use in diagnostic assays and their use as research tools.

The present invention further includes the use of a compound of Formula I to treat neuropsychiatric disorders, preferably a psychosis, more preferably schizophrenia and schizophrenia spectrum disorders. The present invention further includes a use of a compound or a composition of the invention to prepare a medicament for use to treat neuropsychiatric disorders, preferably a psychosis, more preferably schizophrenia and schizophrenia spectrum disorders.

The compounds of the invention can be used alone or in combination with other agents that have antipsychotic activity or in combination with other types of treatment (which may or may not have antipsychotic activity) for psychotic disorders. In a particular aspect of the present invention, the compounds of the invention may be used in combination with other therapies and therapeutics to treat schizophrenia and schizophrenia spectrum disorders.

In addition to the above-mentioned therapeutic uses, the compounds of the invention are also useful in diagnostic assays, screening assays and as research tools.

In a specific embodiment, the present invention provides a method of treating neuropsychiatric disorders, preferably a psychosis, more preferably schizophrenia and schizophrenia spectrum disorders, comprising administering to an animal in need thereof, a therapeutically effective amount of a compound selected from the group of compounds:

(A-1) 8-Trifluoromethyl-11-(4-ethylpiperazin-1-yl)-dibenzo[b,f][1,4]oxazepine;
(A-2) 8-Trifluoromethyl-11-(4-(2'-hydroxyethyl)piperazin-1-yl)-dibenzo[b,f][1,4]oxazepine;
(A-3) 8-Trifluoromethyl-11-(4-propylpiperazin-1-yl)-dibenzo[b,f][1,4]oxazepine;
(A-3a) 8-Trifluoromethyl-11-(4-propylpiperazin-1-yl)-dibenzo[b,f][1,4]oxazepine.HCl;
(A-4) 8-Trifluoromethyl-11-(4-isopropylpiperazin-1-yl)-dibenzo[b,f][1,4]oxazepine;
(A-4a) 8-Trifluoromethyl-11-(4-isopropylpiperazin-1-yl)-dibenzo[b,f][1,4]oxazepine.HCl;
(A-5) 8-Trifluoromethyl-11-(4-butylpiperazin-1-yl)-dibenzo[b,f][1,4]oxazepine;
(A-5a) 8-Trifluoromethyl-11-(4-butylpiperazin-1-yl)-dibenzo[b,f][1,4]oxazepine.HCl;
(A-6) 8-Chloro-11-(4-ethylpiperazin-1-yl)-dibenzo[b,f][1,4]oxazepine;
(A-6a) 8-Chloro-11-(4-ethylpiperazin-1-yl)-dibenzo[b,f][1,4]oxazepine.HCl;
(A-7) 8-Chloro-11-(4-(2'-hydroxyethyl)piperazin-1-yl)-dibenzo[b,f][1,4]oxazepine;
(A-8) 8-Chloro-11-(4-propylpiperazin-1-yl)-dibenzo[b,f][1,4]oxazepine;
(A-9) 8-Chloro-11-(4-isopropylpiperazin-1-yl)-dibenzo[b,f][1,4]oxazepine;
(A-10) 8-Chloro-11-(4-butylpiperazin-1-yl)-dibenzo[b,f][1,4]oxazepine;
(A-11) 8-Fluoro-11-(4-ethylpiperazin-1-yl)-dibenzo[b,f][1,4]oxazepine;
(A-12) 8-Chloro-11-(4-ethylpiperazin-1-yl)-dibenzo[b,f][1,4]thiazepine;
(A-13) 8-Chloro-11-(4-(2'-hydroxyethyl)piperazin-1-yl)-dibenzo[b,f][1,4]thiazepine;
(A-14) 8-Chloro-11-(4-propylpiperazin-1-yl)-dibenzo[b,f][1,4]thiazepine;
(A-14a) 8-Chloro-11-(4-propylpiperazin-1-yl)-dibenzo[b,f][1,4]thiazepine.HCl;
(A-15) 8-Chloro-11-(4-isopropylpiperazin-1-yl)-dibenzo[b,f][1,4]thiazepine.HCl;
(A-15a) 8-Chloro-11-(4-isopropylpiperazin-1-yl)-dibenzo[b,f][1,4]thiazepine.HCl;.
(A-16) 8-Chloro-11-(4-butylpiperazin-1-yl)-dibenzo[b,f][1,4]thiazepine; and
(A-16a) 8-Chloro-11-(4-butylpiperazin-1-yl)-dibenzo[b,f][1,4]thiazepine.HCl.

More specifically the present invention provides a method of treating neuropsychiatric disorders, preferably a psychosis, more preferably schizophrenia and schizophrenia spectrum disorders, comprising administering to an animal in need thereof, a therapeutically effective amount of a compound selected from the group of compounds:

(A-1) 8-Trifluoromethyl-1-(4-ethylpiperazin-1-yl)-dibenzo[b,f][1,4]oxazepine;
(A-2) 8-Trifluoromethyl-11-(4-(2'-hydroxyethyl)piperazin-1-yl)-dibenzo[b,f][1,4]oxazepine;
(A-6) 8-Chloro-11-(4-ethylpiperazin-1-yl)-dibenzo[b,f][1,4]oxazepine,
(A-6a) 8-Chloro-11-(4-ethylpiperazin-1-yl)-dibenzo[b,f][1,4]oxazepine.HCl;
(A-7) 8-Chloro-11-(4-(2'-hydroxyethyl)piperazin-1-yl)-dibenzo[b,f][1,4]oxazepine;
(A-11) 8-Fluoro-11-(4-ethylpiperazin-1-yl)-dibenzo[b,f][1,4]oxazepine;
(A-12) 8-Chloro-11-(4-ethylpiperazin-1-yl)-dibenzo[b,f][1,4]thiazepine; and
(A-13) 8-Chloro-11-(4-(2'-hydroxyethyl)piperazin-1-yl)-dibenzo[b,f][1,4]thiazepine.

Even more specifically, the present invention provides a method of treating neuropsychiatric disorders, preferably a psychosis, more preferably schizophrenia and schizophrenia spectrum disorders, comprising administering to an animal in need thereof, a therapeutically effective amount of a compound selected from the group of compounds:

(A-6) 8-Chloro-11-(4-ethylpiperazin-1-yl)-dibenzo[b,f][1,4]oxazepine;
(A-6a) 8-Chloro-11-(4-ethylpiperazin-1-yl)-dibenzo[b,f][1,4]oxazepine.HCl;
(A-7) 8-Chloro-11-(4-(2'-hydroxyethyl)piperazin-1-yl)-dibenzo[b,f][1,4]oxazepine;
(A-12) 8-Chloro-11-(4-ethylpiperazin-1-yl)-dibenzo[b,f][1,4]thiazepine; and
(A-13) 8-Chloro-1-(4-(2'-hydroxyethyl)piperazin-1-yl)-dibenzo[b,f][1,4]thiazepine.

Most specifically, the present invention provides a method of treating neuropsychiatric disorders, preferably a psychosis, more preferably schizophrenia and schizophrenia spectrum disorders, comprising administering to an animal in need thereof, a therapeutically effective amount of a compound selected from the group of compounds:

(A-6) 8-Chloro-11-(4-ethylpiperazin-1-yl)-dibenzo[b,f][1,4]oxazepine;
(A-6a) 8-Chloro-11-(4-ethylpiperazin-1-yl)-dibenzo[b,f][1,4]oxazepine.HCl; and
(A-7) 8-Chloro-11-(4-(2'-hydroxyethyl)piperazin-1-yl)-dibenzo[b,f][1,4]oxazepine.

Preferably, the animal is a human and the compound is combined with a pharmaceutically acceptable carrier and/or diluent to provide a dosage composition as described hereinbefore.

The following non-limiting examples are illustrative of the present invention:

EXAMPLES

Example 1

8-Trifluoromethyl-11-(4-ethylpiperazin-1-yl)-dibenzo[b,f][1,4]oxazepine

8-Trifluoromethyl-10H-dibenzo[b,f][1,4]oxazepine-11-one (2, X=O, $R^1$=$CF_3$) (2.0 g, 7.16 mmol), phosphorus oxychloride (5 mL, 53 mmol), N,N-dimethylaniline (1.0 ml) and toluene (25 mL) were combined and heated to reflux for 3 hours. The mixture was evaporated under vacuum to afford the imino chloride intermediate A, X=O $R^1$=$CF_3$). This was used in the next step without further purification. Toluene 25 (25 ml) was added followed by 5 ml (45 mmol) of 1-ethylpiperazine. This mixture was refluxed for 3 hours. After evaporation the residue was added to a saturated aqueous $K_2CO_3$, which was extracted with chloroform. The chloroform phase was dried over magnesium sulfate, filtered and the solvent removed to give a viscous liquid. This was purified by flash chromatography on silica gel, eluting with 9:1 hexane:ethyl acetate, then 1:1 hexane:ethyl acetate and finally 100% ethyl acetate. Recrystallization from n-heptane gave the product as yellow crystals, mp 76–77° C., $^1$H NMR (300 MHz, CDCl$_3$) δ1.16 (t, 3H, J=7.2 Hz, CH$_3$), 2.55 (q, 2H, J=7.2 Hz, —CH$_2$—), 2.59 (broad s, 4H, —CH$_2$—), 3.65 (broad s, 4H, —CH$_2$—), 7.20–7.25 (m, 2H), 7.27–7.30 (m, 2H), 7.35–7.39 (dd, J=1.5 and 7.5 Hz, 1H), 7.43 (broad s, 1H), 7.46–7.52 (ddd, J=1.8, 7.2, 8.1 Hz, 1H), MS (EI) m/z 375 (M$^+$, 4.2%), 304 (8.5), 303 (15.1), 292 (5.8), 291 (25.5), 263 (6.9), 262 (18.4), 84 (100), 70 (5.0). HRMS calcd for C$_{20}$H$_{20}$N$_3$OF$_3$ 375.1558, found 375.1557.

Example 2

8-Trifluoromethyl-11-(4-(2'-hydroxyethyl)piperazin-1-yl)-dibenzo[b,f][1,4]oxazepine Prepared in the same manner as Example 1 with 1-(2'-hydroxyethyl)piperazine. mp 110–111° C., $^1$H NMR (300 MHz, CDCl$_3$) δ1.59 (broad s, 1H, —OH), 2.61–2.65 (overlapping broad s and t, 6H), 3.62 (broad s, 4H, —CH$_2$—), 3.67 (t, 2H, —CH$_2$OH), 7.20–7.25 (m, 2H), 7.27–7.30 (m, 2H), 7.35–7.39 (dd, J=1.5 and 7.5 Hz, 1H), 7.43 (broad s, 1H), 7.46–7.52 (ddd, J=1.8, 7.2, 8.1 Hz, 1H), MS (EI) m/z 391 (M$^+$, 2.1%), 292(8.20), 291(34.0), 263 (8.3), 262(22.4), 113(45.1), 101(13.0), 100(100), 70(11.5), 70(9.8). HRMS calcd for C$_{20}$H$_{20}$N$_3$O$_2$F$_3$ 391.1508, found 391.1489.

Example 3

8-Trifluoromethyl-11-(4-propylpiperazin-1-yl)-dibenzo[b,f][1,4]oxazepine.HCl

Prepared in the same manner as Example 1 using 1-propylpiperazine, except that the residue obtained after flash chromatography was dissolved in ethyl acetate and the HCl salt precipitated as a white solid by the addition of 1M HCl in ether. Mp 110 (decomposes), $^1$H NMR (300 MHz, DMSO-d$^6$) δ0.90 (t, 3H, —CH3), 1.17 (m, 2H, —CH$_2$—), 3.02 (m, 6H, piperazine —CH$_2$— and propyl —CH$_2$), 3.51 (broad s, 4H, —CH$_2$), 7.35–7.5 (m, 5H, overlapping Ar—H), 7.57 (dd, 1H, J=1.5 Hz and 7.5 Hz), 7.69 (doublet of triplets, 1H, J=1.5 Hz and 8 Hz), 10.96 (s, 1H, N$^+$H), MS (EI) m/z 389 (M$^+$ for free base, 4.9%), 303 (13.0), 291 (15.9), 193 (9.3), 111 (64.4), 98 (100), 56 (21.7). HRMS calcd for C$_{21}$H$_{22}$N$_3$OF$_3$ 389.1715, found 389.1713.

Example 4

8-Trifluoromethyl-11-(4-isopropylpiperazin-1-yl)-dibenzo[b,f][1,4]oxazepine.HCl

Prepared following the procedure of Example 3 using 1-isopropylpiperazine and had a mp 270° C. (decomposes), $^1$H NMR (300 MHz, DMSO-d$^6$) δ1.20 (d, 6H, J 6.6 Hz), 3.20 (broad s, 4H, —CH$_2$—), 3.45 (overlapping broad s and multiplet, 5H, —CH and —CH$_2$—), 7.35–7.45 (m, 5H, overlapping Ar—H), 7.57 (dd, 1H, J=1.5 Hz and 7.5 Hz), 7.64 (doublet of triplets, 1H, J=1.5 Hz and 8 Hz), 10.8 (s, 1H, N$^+$H), MS (EI) m/z 389 (M$^+$ for free base, 10.4%), 303 (21.0), 291 (16.3), 193 (13.3), 125 (74.1), 111 (58.5), 98 (100), 56 (37.7). HRMS calcd for C$_{21}$H$_{22}$N$_3$OF$_3$ 389.1715, found 389.1715.

Example 5

8-Trifluoromethyl-11-(4-butylpiperazin-1-yl)-dibenzo[b,f][1,4]oxazepine.HCl

Prepared following the procedure of Example 3 with 1-butylpiperazine and had a mp 240° C. (decomposes), $^1$H NMR (300 MHz, DMSO-d$^6$) δ0.91 (t, 3H, J=7.5 Hz, —CH$_3$), 1.31 (m, 2H, —CH$_2$—), 1.65 (m, 2H, —CH$_2$—), 3.10 (broad s, 4H, —CH$_2$), 3.4–3.5 (overlapping multiplets, 6H, piperazinyl —CH$_2$— and butyl N—CH$_2$), 7.35–7.45 (m, 5H, overlapping Ar—H), 7.51 (dd, 1H, J=1.5 Hz and 7.5 Hz), 7.63 (doublet of triplets, 1H, J=1.5 Hz and 8 Hz), 10.2 (s, 1H, N$^+$H), MS (EI) m/z 403 (M$^+$ for free base, 6.3%), 303 (18.5), 291 (17.7), 193 (12.4), 125 (74.1), 112 (100), 70 (37.1), 56 (6.9). HRMS calcd for C$_{22}$H$_{24}$N$_3$OF$_3$ 403.1871, found 403.1858.

Example 6

8-Chloro-11-(4-ethylpiperazin-1-yl)-dibenzo[b,F][1,4]oxazepine (1b) and 8-chloro-11-(4-ethylpiperazin-1-yl)-dibenzo[b,f][1,4]oxazepine.HCl 8-Chloro-10H-dibenzo[b,f][1,4]oxazepin-11-one (2, X=O, R$^1$=Cl) (6.0 g, 24.4 mmol), phosphorus oxychloride (20 mL, 212 mmol), N,N-dimethylaniline (3.0 ml) and toluene (100 mL) were combined and heated to reflux for 3 hours. After evaporation, the residue was dissolved in 50 mls of toluene, 21.7 ml (170 mmol) of 1-ethylpiperazine was added and the mixture was refluxed for 3 hours. After evaporation, the residue was added to saturated aqueous K$_2$CO$_3$, which was extracted with chloroform. The chloroform phase was dried over MgSO$_4$, and after filtration the chloroform was evaporated to give a viscous liquid which was purified by flash chromatography on silica gel (9:1 hexane:ethyl acetate, then 1:1 hexane:ethyl acetate and finally 100% ethyl acetate). The crude free base form of the product was a low melting solid that had $^1$H NMR (300 MHz, CDCl$_3$) δ 1.13 (t, 3H, CH$_3$), 2.45–2.60 (broad m, 6H, piperazinyl CH$_2$ and ethyl CH$_2$), 3.65 (broad s, 4H, CH$_2$), 6.92 (dd, 1H, J=2.5 and 8.5 Hz), 7.08 (d, 1H, J=8.5 Hz), 7.14 (d, 1H, J=2.5 Hz), 7.22 (doublet of triplets, 1H, J=1.6 and 7.6 Hz), 7.25 (dd, 1H, 1.4 and 8.1 Hz), 7.36 (dd, 1H, J=1.9 and 7.7 Hz), 7.48 (ddd, 1H, J=1.9, 7.7, 8.1 Hz). The solid was converted to the HCl salt by dissolving in ethyl acetate and adding 1N HCl. This gave a white solid (3.8 g, 43%), mp. 280 (decomposes), $^1$H NMR (300 MHz, DMSO-d$^6$) δ 1.24 (t, 3H, —CH$_3$), 3.18 (q, 2H, CH$_2$), 3.2–3.3 (broad, 4H, piperazinyl CH$_2$), 3.6–3.7 (Broad, 4H, piperazinyl CH$_2$), 7.07–7.13 (2H, m, overlapping coupled pair), 7.26 (dd, 1H, J=0.9 and 8.0 Hz), 7.36 (doublet of triplets, 1H, J=1.5 and 8.2 Hz), 7.43 (dd, 1H, 1.2 and 8.1 Hz), 7.52 (dd, 1H, 1.8 and 8.4 Hz), 7.64 (ddd, 1H, J=1.8, 8.0 and 8.4 Hz), MS (EI) m/z 341 (M$^+$ for free base, 14.9%), 269(15.3), 257(41.5), 228 (6.8), 193(24.3), 97(85.4), 84(100), HRMS calcd for C$_{19}$H$_{20}$N$_3$OCl 341.1295, found 341.1297.

Example 7

8-Chloro-11-(4-(2'-hydroxyethyl)piperazin-1-yl)-dibenzo[b,f][1,4]oxazepine

This was prepared in the same manner as Example 6 using 1-(2'-hydroxyethylpiperazine). The free base obtained by flash chromatography was recrystallized from 10:1 hexane-:ethyl acetate to give yellow crystals of mp 149–150° C., $^1$H NMR (300 MHz, CDCl$_3$), δ 1.66 (s, 1H, OH), 2.65–2.75 (m, 6H, overlapping —CH$_2$— peaks), 3.62 (broad s, 4H, piperazinyl CH$_2$), 3.68 (t, 2H, J=5.4 Hz), 6.92 (dd, 1H, J=2.5 and 8.5 Hz), 7.04 (d, 1H, J=8.5 Hz), 7.12 (d, 1H, J=2.5 Hz), 7.20 (doublet of triplets, 1H, J=1.6 and 7.6 Hz), 7.24 (dd, 1H, 1.4 and 8.1 Hz), 7.34 (dd, 1H, J=1.9 and 7.7 Hz), 7.46 (ddd, 1H, J=1.9, 7.7, 8.1 Hz), MS (EI) m/z 357 (M$^+$, 2.0%), 229(6.5), 228(21.6), 113(45.9), 101(10.7), 100(100), 70(10.1), 69(10.8), HRMS calcd for C$_{19}$H$_{20}$N$_3$O$_2$Cl 357.1244, found 357.1254.

Example 8

8-Chloro-11-(4-propylpiperazin-1-yl)-dibenzo[b,f][1,4]oxazepine

Prepared in the same manner as Example 7 with 1-propylpiperazine and had a mp 90–91° C., $^1$H NMR (300

MHz, CDCl$_3$), δ 0.93 (t, 3H, J=7.7 Hz, CH$_3$), 1.58 (m, 2H, CH$_2$), 2.39, (t, 2H, CH$_2$N), 2.55–2.65 (broad s, 4H, piperazinyl CH$_2$), 3.55–3.65 (broad s, 4H, piperazinyl CH$_2$), 6.89 (dd, 1H, J=2.5 and 8.5 Hz), 7.03 (d, 1H, J=8.5 Hz), 7.12 (d, 1H, J=2.5 Hz), 7.21 (doublet of triplets, 1H, J=1.6 and 7.6 Hz), 7.24 (dd, 1H, 1.4 and 8.1 Hz), 7.33 (dd, 1H, J=1.9 and 7.7 Hz), 7.45 (ddd, 1H, J=1.9, 7.7, 8.1 Hz), MS (EI) m/z 355 (M$^+$, 11.0%), 269(15.7), 257(32.1), 228(15.7), 193(21.5), 111(80.3), 98(100), HRMS calcd for C$_{20}$H$_{22}$N$_3$OCl 355.1451, found 355.1457.

Example 9

8-Chloro-11-(4-isopropylpiperazin-1-yl)-dibenzo[b,f][1,4]oxazepine

Prepared in the same manner as Example 7 with 1-isopropylpiperazine and had a mp 55–56° C., $^1$H NMR (300 MHz, CDCl$_3$), δ 1.08 (d, 6H, J=6.6 Hz, CH$_3$), 2.55–2.65 (broad s, 4H, piperazinyl CH$_2$), 2.74 (septet, 1H, J=6.6 Hz, CH), 3.55–3.65 (broad s, 4H, piperazinyl CH$_2$), 6.89 (dd, 1H, J=2.5 and 8.5 Hz), 7.02 (d, 1H, J=8.5 Hz), 7.12 (d, 1H, J=2.5 Hz), 7.19 (doublet of triplets, 1H, J=1.6 and 7.6 Hz), 7.24 (dd, 1H, 1.4 and 8.1 Hz), 7.33 (dd, 1H, J=1.9 and 7.7 Hz), 7.44 (ddd, 1H, J=1.9, 7.7, 8.1 Hz), MS (EI) m/z 355 (M$^+$, 7.8%), 269(15.7), 257 (17.0), 245(10.8), 228(11.8), 193(19.7), 111(61.0), 98(100), 56 (46.5), HRMS calcd for C$_{20}$H$_{22}$N$_3$OCl 355.1451, found 355.1470.

Example 10

8-Chloro-11-(4-butylpiperazin-1-yl)-dibenzo[b,f][1,4]oxazepine

Prepared in the same manner as Example 7 with 1-butylpiperazine and had a mp 97–98° C., $^1$H NMR (300 MHz, CDCl$_3$), δ 0.93 (t, 3H, J=7.5 Hz, CH$_3$), 1.35 (sextet, 2H, CH$_2$), 1.46 (quintet, 2H, CH$_2$), 2.40 (t, 2H, NCH$_2$), 2.55–2.65 (broad s, 4H, piperazinyl CH$_2$),3.55–3.65 (broad s, 4H, piperazinyl CH$_2$), 6.89 (dd, 1H, J=2.5 and 8.5 Hz), 7.02 (d, 1H, J=8.5 Hz), 7.12 (d, 1H, J=2.5 Hz), 7.19 (doublet of triplets, 1H, J=1.6 and 7.6 Hz), 7.24 (dd, 1H, 1.4 and 8.1 Hz), 7.33 (dd, 1H, J=1.9 and 7.7 Hz), 7.44 (ddd, 1H, J=1.9, 7.7, 8.1 Hz), MS (EI) m/z 369 (M$^+$, 8.7%), 291 (30.5), 269 (15.1), 257 (24.8), 228(13.8), 193(25.0), 125(78.9), 112 (100), 70(40.9), HRMS calcd for C$_{21}$H$_{24}$N$_3$OCl 369.1608, found 369.1604.

Example 11

8-Fluoro-11-(4-ethylpiperazin-1-yl)-dibenzo[b,f][1,4]oxazepine

Prepared in the same manner as Example 1 starting with 8-fluoro-10H-dibenzo[b,f][1,4]oxazepin-11-one (2, X=O, R$^1$=F) with 1-ethyl piperazine. This compound was an oil with $^1$H NMR (400 MHz, CDCl$_3$), δ1.16 (t, 3H, J=7.2 Hz, CH$_3$), 2.55 (q, 2H, J=7.2 Hz, —CH$_2$—), 2.55–2.65 (broad s, 4H, piperazinyl CH$_2$) 3.55–3.65 (broad s, 4H, piperazinyl CH$_2$), 6.64 (ddd, 1H, J=2.4, 6.6 and 7.2 Hz), 6.82 (dd, 1H, J=2.1 and 7.5 Hz), 7.12 (dd, 1H, J=4.2 and 6.2 Hz), 7.21 (doublet of triplets, 1H, J=0.8 and 6.0 Hz), 7.23 (dd, 1H, J=0.9 and 6.3 Hz), 7.34 (dd, 1H, J=1.2 and 5.7 Hz), 7.44 (doublet of triplets, 1H, J=1.2 and 6.0 Hz).

Example 12

8-Chloro-11-(4-ethylpiperazin-1-yl)-dibenzo[b,f][1,4]thiazepine

8-Chloro-10H-dibenzo[b,f][1,4]thiazepin-11-one 2 (X=S and R$^1$=Cl) (0.5 g, 1.91 mol), phosphorus oxychloride (5 ml, 53 mmol), toluene (25 ml) and N,N-dimethylaniline (1.0 ml) were heated at reflux for 3 hours. After evaporation of the volatiles, 25 ml of toluene and 5 ml (45 mmol) of 1-ethylpiperazine were added. Work-up and purification as described in Example 1 gave 150 mg (22%) of light yellow crystals, mp 100–101° C., $^1$H NMR (300 MHz, CDCl$_3$), δ1.11 (t, 3H, J=6.0 Hz, CH$_3$), 2.55 (q, 2H, J=6.0 Hz, —CH$_2$—), 2.55–2.65 (broad s, 4H, piperazinyl CH$_2$), 3.55–3.65 (broad s, 4H, piperazinyl CH$_2$), 6.83 (dd, 1H, J=1.5 and 6.0 Hz), 7.07 (d, 1H, J=1.5 Hz), 7.25–7.40 (mult., 4H), 7.50 (dd, 1H, J=7.5 Hz), MS (EI) m/z 357 (M$^+$, 16.1%), 244(34.2), 209(30.1), 97(93.7), 84(100), HRMS calcd for C$_{19}$H$_{20}$N$_3$SCl 357.1066, found 357.1067.

Example 13

8-Chloro-11-(4-(2'-hydroxyethyl)piperazin-1-yl)-dibenzo[b,f][1,4]thiazepine

Prepared following the procedure of Example 12 using 1-(2'-hydroxyethyl)piperazine and had mp 110–111° C., $^1$H NMR (300 MHz, CDCl$_3$), δ 2.55–2.65 (broad s, 4H, piperazinyl CH$_2$), 2.64 (t, 2H, J=7.5 Hz, CH$_2$—), 3.55–3.65 (broad s, 4H, piperazinyl CH$_2$), 3.68 (t, 2H, J=7.5 Hz, —CH$_2$OH), 6.88 (dd, 1H, J=1.5 and 6.0 Hz), 7.11 (d, 1H, J=1.5 Hz), 7.30–7.40 (mult., 4H), 7.54 (dd, 1H, J=7.5 Hz), MS (EI) m/z 373 (M$^+$, 6.1%), 244(53.9), 209(47.0), 113 (42.0), 100(100), HRMS calcd for C$_{19}$H$_{20}$N$_3$OSCl Example 14

8-Chloro-11-(4-propylpiperazin-1-yl)-dibenzo[b,f][1,4]thiazepine.HCl

Prepared using the procedure of Example 12 using 1-propylpiperazine, the HCl salt being obtained by dissolving the residue obtained from flash chromatography in ethyl acetate and precipitating the salt with 1N HCl in ether. The salt was a hygroscopic white solid with $^1$H NMR (300 MHz, DMSO-d$^6$), δ 0.90 (t, 3H, CH$_3$), 1.70 (m, 2H, —CH$_2$—), 3.00 (t, 2H, —CH$_2$N), 3.0–3.1 (broad s, 4H, piperazinyl CH$_2$), 3.5–3.6 (broad s, 4H, piperazinyl CH$_2$), 7.00 (dd, 1H, J=2.1 and 8.4 Hz), 7.07 (d, 1H, J=2.1 Hz), 7.40 (d, 1H, J=8.4 Hz), 7.5–7.6 (m, 4H), 10.7 (s, 1H, N$^+$H), MS (EI) m/z 371 (M$^+$ for free base, 55.1%), 286(51.0), 244 (30.2), 209(23.6), 111 (19.1), 97(100), HRMS calcd for C$_{20}$H$_{22}$N$_3$SCl 371.1223, found 371.1233.

Example 15

8-Chloro-11-(4-isopropylpiperazin-1-yl)-dibenzo[b,f][1,4]thiazepine.HCl

Prepared using the procedure of Example 12 using 1-isopropylpiperazine, the HCl salt being obtained by dissolving the residue obtained from flash chromatography in ethyl acetate and precipitating the salt with 1N HCl in ether. The salt had a mp 140 (decomposes), 1$^1$H NMR (300 MHz, DMSO-d$^6$), δ 1.31 (d, 6H, CH$_3$), 3.0–3.1 (broad s, 4H, piperazinyl CH$_2$), 3.3 (septet, 1H, CH), 3.5–3.6 (broad s, 4H, piperazinyl CH$_2$), 7.02 (dd, 1H, J=2.1 and 8.4 Hz), 7.11 (d, 1H, J=2.1 Hz), 7.43 (d, 1H, J=8.4 Hz), 7.5–7.6 (m, 4H), 11.0 (s, 1H, N$^+$H), MS (EI) m/z 371 (M$^+$ for free base, 7.2%), 286(13.1), 244 (18.6), 209(25.7), 111 (66.8), 98(100), HRMS calcd for C$_{20}$H$_{22}$N$_3$SCl 371.1223, found 371.1234.

Example 16

8-Chloro-11-(4-butylpiperazin-1-yl)-dibenzo[b,f][1,4]thiazepine.HCl

Prepared using the procedure of Example 12 using 1-butylpiperazine, the HCl salt being obtained by dissolving the residue obtained from flash chromatography in ethyl acetate and precipitating the salt with 1N HCl in ether. The salt was a hygroscopic white solid and $^1$H NMR (300 MHz, DMSO-d$^6$), δ 0.99 (t, 3H, CH$_3$), 1.33 (2H, m), 1.69 (2H, m), 3.02 (t, 2H, NCH$_2$, 3.1–3.2 (broad s, 4H, piperazinyl CH$_2$), 3.5–3.6 (broad s, 4H, piperazinyl CH$_2$), 7.02 (dd, 1H, J=2.1 and 8.4 Hz), 7.11 (d, 1H, J=2.1 Hz), 7.43 (d, 1H, J=8.4 Hz), 7.5–7.6 (m, 4H), 9.9 (s, 1H, N$^+$H).

TABLE 1

Summary of Examples for Compounds of Formula 1

I

| Example # | R$^1$ | R$^2$ | X |
|---|---|---|---|
| 1 | CF$_3$ | CH$_2$CH$_3$ | O |
| 2 | CF$_3$ | CH$_2$CH$_2$OH | O |
| 3 | CF$_3$ | CH$_2$CH$_2$CH$_3$ | O |
| 4 | CF$_3$ | CH(CH$_3$)$_2$ | O |
| 5 | CF$_3$ | CH$_2$CH$_2$CH$_2$CH$_3$ | O |
| 6 | Cl | CH$_2$CH$_3$ | O |
| 7 | Cl | CH$_2$CH$_2$OH | O |
| 8 | Cl | CH$_2$CH$_2$CH$_3$ | O |
| 9 | Cl | CH(CH$_3$)$_2$ | O |
| 10 | Cl | CH$_2$CH$_2$CH$_2$CH$_3$ | O |
| 11 | F | CH$_2$CH$_3$ | O |
| 12 | Cl | CH$_2$CH$_3$ | S |
| 13 | Cl | CH$_2$CH$_2$OH | S |
| 14 | Cl | CH$_2$CH$_2$CH$_3$ | S |
| 15 | Cl | CH(CH$_3$)$_2$ | S |
| 16 | Cl | CH$_2$CH$_2$CH$_2$CH$_3$ | S |

Example 17

8-Trifluoromethyl-10H-dibenzo[b,f][1,4]oxazepin-11-one (Formula 2, X=O, R$^1$=CF$_3$)

(a) Methyl salicylate (30.4 g, 0.20 mol), 4-fluoro-3-nitrobenzotrifluoride (41.8 g, 0.20 mol), 18-crown-6 (10.6 g, 0.04 mol), 40% w.w potassium fluoride-alumina and acetonitrile (200 ml) were refluxed for 4 hours. After cooling, 500 mls each of water and diethyl ether were added, and the mixture was transferred to a separatory funnel. After vigorous mixing the aqueous layer and alumina sediments were discarded, and the organic phase was washed twice with 200 mls of saturated potassium chloride solution. The organic layer was dried over MgSO$_4$, and after filtration, the volatiles were removed by rotary evaporator to give 50.9 g (74.6% yield) of methyl O-(2-nitro-4-trifluoromethylphenyl)salicylate, mp 56–57° C., $^1$H NMR (300 MHz, CDCl$_3$), δ 3.75 (s, 3H), 6.82 (d, 1H, J=8.7 Hz), 7.21 (d, 1H, J=8.7 Hz), 7.40 (t, 1H, J=7.8 Hz), 7.63–7.67 (m, 2H), 8.06 (dd, 1H, J=1.2 Hz, J=6.0 Hz), 8.25 (d, 1H, J=1.5 Hz).

(b) Methyl O-(2-nitro-4-trifluoromethylphenyl)salicylate (30.0 g, 0.088 mol) was dissolved in 150 ml of methanol and hydrogenated over Raney nickel (7.5 g) at room temperature and 50 psi pressure for 6 hours. After filtration to remove the catalyst, the methanol was removed and the residue dissolved in tetrahydrofuran (50 ml) and methanol (50 ml), followed by treatment with 5 N NaOH (20 ml) for 3 hours. After concentration in vacuo, the residue was acidified to pH 1–2 with 6 N HCl. The resulting suspension was filtered to give a solid which was recrystallized from n-heptane to provide O-(2-amino-4-trifluoromethylphenyl)salicylic acid as light gray solid, 13.3 g, 50.9%, mp 108–109.

(c) The aminosalicylic acid (17.3 g, 58.2 mmol) was refluxed in 150 ml of xylene for 24 hours with continuous removal of water. The xylene was removed, and the residue was recrystallized from methanol to provide 8-trifluoromethyl-10H-dibenzo[b,f][1,4]oxazepin-11-one as a white solid, mp 246–247° C., $^1$H NMR (DMSO-d$^6$), δ 7.38–7.66 (m, 7H), 10.7 (s, 1H, NH).

Example 18

8-Chloro-10H-dibenzo[b,f][1,4]oxazepin-11-one (Formula 2, X=O, R$^1$=Cl)

(a) Salicylaldehyde (0.386 mol) was dissolved in anhydrous DMF (300 ml), and allowed to react with 6.84 g of sodium hydride (95%, 0.27 mol). After the reaction was complete, 2,5-dichloronitrobenzene (40 g, 0.208 mol) was added all at once, and the reaction mixture was stirred at 95–100° C. for 22 hours. The DMF is removed and the residue was extracted with 800 mL dichloromethane. The organic phase was washed with 1N NaOH (2×500 mL), dried over MgSO$_4$ and evaporated to a brown solid of O-(2-nitro-4-chlorophenyl)salicylaldehyde (48.5 g, 83.9%), m.p. 82–83° C., $^1$H NMR (300 MHz, CDCl$_3$), δ 6.88 (d, 1H, J=8.1 Hz), 7.06 (d, 1H, J=9.0 Hz,), 7.31 (t, 1H, J=7.5 Hz), 7.54 (qd, 2H, J=1.2 Hz, J=2.4 Hz), 7.97 (dd, 1H, J=1.8 Hz, J=7.8 Hz), 8.04 (d, 1H, J=2.4 Hz), 10.45(d, 1H, J=0.9 Hz, —CHO).

(b) To a stirred solution of 48.5 g of O-(2-nitro-4-chlorophenyl)salicylaldehyde in 200 mL of acetone at room temperature was added 180 mL of chromic acid reagent (100 g Na$_2$Cr$_2$O$_7$, 153 g of concentrated H$_2$SO, and sufficient H$_2$O to make 500 ml total volume) over a period of 15 min. The solution was kept at 50° C. by cooling during the addition. After the addition was complete, the mixture was stirred for 20 hours. The acetone was removed, the residue was added into a saturated Na$_2$CO$_3$ solution. After filtration, the filtrate was neutralized with concentrated HCl to provide a yellow solid of O-(2-nitro-4-chlorophenyl)salicylic acid, 33.74 g (65.8%), mp 155–160°, $^1$H NMR (300 MHz, CDCl3), δ 6.887 (d, 1H, J=9.0 Hz), 7.04 (dd, 1H, J=0.9 Hz, J=8.1 Hz), 7.36 (t, 1H, J=8.1 Hz), 7.48 (dd, 1H, J=2.7 Hz, J=9.0 Hz), 7.60 (dd, 1H, J=1.5 Hz, J=8.1 Hz), 8.01(d, 1H, J=2.4 Hz), 8.15 (dd, 1H, J=1.8 Hz, J=8.1 Hz).

(c) A solution of 33.74 g of O-(2-nitro-4-chlorophenyl) salicylic acid in 150 mL of methanol was hydrogenated over Raney nickel (6.8 g) at room temperature and 30 psi pressure with stirring for 20 hours. The crude amino acid obtained on evaporation of the methanol was refluxed in 150 mL of xylene for 20 hours with continuous removal of water. The xylene solution was cooled and the xylene was removed, the residue was washed with THF, filtered and dried to provide 8-chloro-10H-dibenzo[b,f][1,4]oxazepin-11-one as gray solid (13.3 g, 40%), mp 260–261°. 1H NMR (300 MHz, DMSO-d$^6$), δ 7.15–7.2 (m, 2H), 7.3–7.4 (m, 3H), 7.64 (ddd, 1H, J=1.9, 7.8 and 8.4 Hz), 7.78 (dd, 1H, J=1.5 and 7.7 Hz), 10.589 (s, 1H, —NH).

Example 19

8-Fluoro-10H-dibenzo[b,f][1,4]oxazepin-11-one (Formula 2, X=O, R$^1$=F)

This was obtained following the procedure of Example 18 using 2,5-difluoronitrobenzene in place of 2,5-dichloronitrobenzene in step (a). The intermediate O-(2- nitro-4-fluorophenyl)salicylaldehyde had a $^1$H NMR (300 MHz, CDCl$_3$) ☐ 6.82 (d, 1H, J=8.4 Hz), 7.15–7.40 (m, 3H), 7.54 (ddd, 1H, J=1.9, 7.6 and 8.1 Hz), 7.81 (dd, 1H, 2.3 and 7.6 Hz), 7.97 (dd, 1H, J=1.7 and 8.8 Hz), 10.50 (d, 1H, J=0.9 Hz, —CHO). The intermediate O-(2-nitro-4-fluorophenyl) salicylic acid had a $^1$H NMR (300 MHz, CDCl$_3$) ☐ 6.95–7.05 (m, 2H), 7.25–7.35 (m, 2H), 7.60 (ddd, 1H, J=1.9, 7.6 and 8.1 Hz), 7.79 (dd, 1H, 2.7 and 7.6 Hz), 8.16 (dd, 1H, J=1.5 and 8.6 Hz). 8-Fluoro-10H-dibenzo[b,f][1,4]oxazepin-11-one had a mp 228–229° C. and $^1$H NMR (300 MHz, DMSO-d$^6$), δ 6.95–7.05 (m, 2H), 7.31–7.42 (m, 3H), 7.60 (ddd, 1H, J=1.8, 7.6 and 8.12 Hz), 7.79 (dd, 1H, J=1.3 Hz and 7.7 Hz), 10.64 (s, 1H, —NH).

Example 20

8-Chloro-10H-dibenzo[b,f][1,4]thiazepin-11-one (Formula 2, X=S, R$^1$=Cl)

(a) Methyl thiosalicylate (5.0 g, 0.0297 mol ) was dissolved in a solution of sodium hydroxide 1.18 g (0.030 mol) in water (2.5 mL) and methanol (60 mL). To the resulting red solution was added 6.9 g (0.036 mol) of 2,5-dichloronitrobenzene dissolved in methanol (20 mL). The mixture was refluxed for 23 h. The reaction mixture was cooled to room temperature, partitioned between equal parts diethyl ether and water, and shaken vigorously. The aqueous layer was drawn from the funnel, and the resulting organic phase was dried over MgSO$_4$, filtered, and concentrated in vacuo to provide yellow crystals of methyl S-(2-nitro-4-chloromethylphenyl)thiosalicylate (9.13 g, 95%), $^1$H NMR (300 MHz, CDCl$_3$), δ 3.822 (s, 3H, —OCH$_3$), 6.95 (d, 1H), 7.26 (s, 1H), 7.49 (dd, 1H, J=1.5 Hz), 7.45–7.47 (m, 2H), 7.90 (dd, 1H), 8.12 (d, 1H).

(b) A solution of 9.0 g (27.8 mmol) of methyl S-(2-nitro-4-chloromethylphenyl)thiosalicylate in 100 mL of methanol was hydrogenated over Raney nickel (1.12 g) at room temperature and 30 psi pressure with stirring for 17 hours. The residue obtained on evaporation of the methanol was dissolved in chloroform, filtered, dried over MgSO$_4$, filtered, and concentrated in vacuo to provide methyl S-(2-amino-4-chloromethylphenyl)thiosalicylate as a white solid (8.16 g, 55.6%), $^1$H NMR (300 MHz, CDCl$_3$) δ 4.00 (s, 3H, —OCH$_3$), 4.40 (s, 2H, —NH$_2$), 6.77 (dd, 1H, J=1.2 Hz), 6.79 (dd, 1H, J=2.1 Hz), 6.84 (dd, 1H, J=2.4 Hz), 7.15–7.20 (m, 1H), 7.28–7.34 (m, 1H), 7.40 (d, 1H, J=8.1 Hz), 8.006 (dd, 1H, J=1.5 Hz).

(c) 8.16 g Methyl S-(2-amino-4-chloromethylphenyl)thiosalicylate was dissolved in THF (50 mL) and methanol (50 mL), and treated with 5N sodium hydroxide solution (20 mL) with stirring at room temperature for 17 h. The reaction mixture was concentrated in vacuo, diluted with water, and acidified to pH 1–2 with 6N hydrochloric acid. The resulting suspension was filtered, and recrystallized from n-heptane to provide S-(2-amino-4-chloromethylphenyl)thiosalicylic acid as a light gray solid, $^1$H NMR (300 MHz, CDCl$_3$), δ 6.77 (dd, 1H, J=2.7 Hz, J=2.1 Hz), 6.83 (d, 1H, J=2.1 Hz), 7.18 (t, 1H), 7.367 (s, 1H), 7.32 (t, 1H), 7.38 (d, 1H, J=8.4 Hz), 8.13 (d, 1H, J=1.8 Hz).

(d) S-(2-Amino-4-chloromethylphenyl)thiosalicylic acid was refluxed in 150 mL of xylene for 21 h with continuous removal of H$_2$O. The xylene was removed, the residue was washed with 95% ethanol, filtered and dried to provide 8-chloro-10H-dibenzo[b,f][1,4]thiazepin-11-one as a white solid of mp 163–165° C., $^1$H NMR (300 MHz, DMSO-d$^6$),δ 7.22 (dd, 1H, J=2.4 and 8.5 Hz), 7.28 (d, 1H, J=2.4 Hz), 7.44–7.53 (m, 3H), 7.58 (d, 1H, J=8.4 Hz), 7.68 (m, 1H), 10.80 (s, 1H).

Example 21

Binding Affinity and K$_{off}$

A desirable feature of a compound of the present invention is a low affinity and a fast K$_{off}$ (as predicted by low affinity). As mentioned hereinabove a preferred affinity (K$_i$) is above about 40 nM. Compounds of the invention have been tested for their affinity using the methods described in Seeman et al. (1993) using $^3$H-raclopride as ligand. The results are provided in Table 2.

TABLE 2

Summary of Binding Data

| Example Number | K$_i$ (nM) |
|---|---|
| 1 | 258 |
| 2 | 414 |
| 3 | n/a |
| 4 | 215 |
| 5 | 250 |
| 6 | 42 |
| 7 | 108 |
| 8 | 23 |
| 9 | 150 |
| 10 | 28 |
| 11 | n/a |
| 12 | 63 |
| 13 | 88 |
| 14 | n/a |
| 15 | 58 |
| 16 | n/a |

| K$_i$ values of various compounds for comparison | |
|---|---|
| Isoloxapine | 20 |
| Loxapine | 9.8 |
| Isoclozapine | 15 |
| Clozapine | 76 | n/a = not available.

Example 22

D$_2$ Receptor Occupancy and Catalepsy

To document the fact that the compounds cross the blood brain barrier, occupancy at the dopamine D$_2$ receptors using in-vivo occupancy measures was examined in rats. The test compound was injected subcutaneously followed 30 minutes later by an intravenous injection of $^3$H-raclopride. The animals were sacrificed 1 hour after drug administration. In animals combining occupancy and catalepsy, rats were tested for catalepsy 10 minutes before sacrifice. Animals were sacrificed by decapitation. Striata and cerebella were rapidly dissected, processed and analyzed as described by Kapur et al. (2000b) Compounds which crossed the blood brain barrier and gave predictable dose-response relationships were then tested to see if they gave catalepsy. Catalepsy is the time-honoured animal model to predict the propensity of compounds to give rise to extrapyramidal side-effects in humans. Catalepsy was measured using a grid-test by a rater blind to the treatment-assignment. The time that animals remained immobile was used as an index of catalepsy by transforming raw-scores into catalepsy scores, with a score of 1 as questionable catalepsy and scores of 2–5 reflecting severity of catalepsy (Ahlenius S et al. 1986). To validate this procedure it was first documented that haloperidol (a drug known to give rise to motor side-effects in humans) gave rise to robust catalepsy at doses above 0.25 mg/kg/sc while clozapine (a drug known not to give rise to motor side-effects in humans) did not give rise to catalepsy at doses up to 20 mg/kg/sc.

The compound of Example 6 showed a dose-dependent increase in D$_2$ occupancy (dose 1–40 mg/kg/sc in acidified saline; occupancy 5–81%, with an ED$_{50}$ of about 5 mg/kg). No animals showed any evidence of motor-side-effects with this compound.

The compound of Example 7 showed a dose-dependent increase in D$_2$ occupancy (dose 1–40 mg/kg/sc in acidified saline; occupancy 22–75% with an $ED_{50}$ of 10 mg/kg). No animals showed any evidence of motor-side-effects in doses up to 40 mg/kg/sc with this compound.

Example 23

Conditioned Avoidance Response

All antipsychotics show an inhibition of the conditioned "avoidance" response (CAR) at doses which do not cause catalepsy and do not cause escape deficits. Therefore the new compounds were tested for activity in this model. For conditioned avoidance-response, rats were trained and tested in a computer assisted two-way active avoidance (shuttlebox), with an 80 dB white-noise as a conditioned stimulus, followed ten seconds later by a 0.6 mA shock as the unconditioned stimulus. Details of the procedure have been described elsewhere (Wadenberg M L et al. 2000). The tests were first validated by documenting that haloperidol (>0.05 mg/kg/sc) and clozapine (>10 mg/kg/sc) gave rise to robust inhibition of avoidance, without catalepsy or escape deficits.

The compound of Example 6 showed >50% inhibition of CAR at doses of 10 mg/kg/sc. The compound of example 7 showed >50% inhibition of CAR at doses of 20 mg/kg/sc.

Example 24

FOS Immunohistochemistry

It is thought that drug-induced immediate-early-gene product FOS provides a valid marker for identifying antipsychotics that do not give rise extrapyramidal side-effects. In particular, all antipsychotics induce FOS in the nucleus accumbens regions while those likely to give rise to motor side-effects also induce FOS in the dorsolateral striatum (Robertson et al. 1994). For examining the distribution of FOS protein by the test compound, the test compound was injected into rats and two hours later, the animals were deeply anaesthetized with sodium phenobarbitol (100 mg/kg i.p.) and perfused transcardially, the brains removed and post-fixed. Immunostaining was performed on free-floating forty-micron sections with a rabbit-raised polyclonal primary anti-FOS antiserum (diluted 1:250 and incubated 48 hours at 4° C.) (4–17 aminoacids of human Fos; Oncogene Research Products, Cambridge, Mass., USA). Exposure to a biotinylated goat anti-rabbit secondary antibody (1:600, Vector Laboratories, Burlingame, Calif., USA) followed by incubation with horseradish peroxidase avidin-biotin complex (Vector Laboratories, Vector Laboratories, Burlingame, Calif., USA) was used to visualize the FOS staining. Fos-immunoreactive nuclei were counted within 400×400 $\mu$m grid at a magnification of 100× in the shell of nucleus accumbens and dorsolateral striatum. This procedure was validated by showing that both haloperidol and clozapine gave robust FOS induction in the nucleus accumbens, but only haloperidol resulted in FOS in the dorsolateral striatum. In tests for FOS protein induction, the compound of Example 6 showed robust induction of FOS protein in the nucleus accumbens, with no induction of FOS protein in the dorsolateral striatum.

Index of Patents

| No. | Patent No. | Issue Date | Title |
|---|---|---|---|
| 1. | 3,347,849 | Oct. 17, 1967 | 5-(Basic Substituted)-Dibenzodiazepines |
| 2. | 3,367,930 | Feb. 6, 1968 | Process for the Preparation of Heterocyclic Compounds |
| 3. | 3,412,193 | Nov. 19, 199/ | 11-(4-Methyl-1-Piperazinyl)dibenz[b,f][1,4]Oxazepines or Thiazepines for Controlling Fertility |
| 4. | 3,444,169 | May 13, 1969 | Process for 11-Aminodibenzo[bf,][1,4]Oxazepines and Analogous Thiazepines |
| 5. | 3,539,573 | Nov. 10, 1970 | 11-Basic Substituted Dibenzodiazepines and Dibenzothiazepines |
| 6. | 3,546,226 | Dec. 8, 1970 | 11-Basic Substituted Dibenzoxazepines |
| 7. | 3,663,696 | May 16, 1972 | Treatment of Depression With 2-Chloro-11-(Piperazinyldibenz-[b,f][1,4]Oxazepines and Acid Addition Salts Thereof |
| 8. | 3,681,357 | Aug. 1, 1972 | 2-Chloro-11-(Piperazinyl)Dibenzy[b,f][1,4]Oxazepine and Acid Addition Salts Thereof |
| 9. | 5,068,437 | Nov. 26, 1991 | Process for Producing 2-(P-Chlorophenoxy) Aniline |
| 10. | 5,393,752 | Feb. 28, 1995 | Methylpiperazinoazepine Compounds, Preparation and Use Thereof |
| 11. | 5,602,120 | Feb. 11, 1997 | Benzyl-Substituted Compounds Having Dopamine Receptor Affinity |
| 12. | WO 99/31267 | Dec. 18, 1998 | Methods for the Simultaneous Identification of Novel Biological Targets and Lead Structures for Drug Development |
| 13. | 436 297 [CH] | May 31, 1967 | Verfahren zur Herstellung 11-Basich substituierter Dibenz[b,f]-[1,4]oxazepine |
| 14. | 1,164,360 [GB] | Nov. 30, 1967 | A Process for Preparing Tricyclic Organic Compounds |

Index of Articles

| No. | Author | Title | Citation |
|---|---|---|---|
| 15. | Ahlenius, S., et al. | Involvement of Extrapyramidal Motor Mechanisms in the Suppression of Locomotor Activity by Antipsychotic Drugs: A Comparison Between the Effects Produced by Pre- and Post-Synaptic Inhibition of Dopaminergic Neurotransmission | Pharmac., Biochem. & Behavior, Vol. 24, PP. 1409–1415 (986) (Ahlenius S et al. 1986) |

-continued

| | | | |
|---|---|---|---|
| 16. | Bartl, V., et al. | Neurotropic and Psychotropic Agents. LXV: 8-Chloro and 8-Isopropyl-6-Piperazinobenzo(b)Pyrido[3,2-f] Thiepin | Collection Czech. Chem. Community (Vol. 38), pp. 2778–2787 (1973) |
| 17. | Bartl, V., et al. | Neurotropic and Psychotropic Agents. LXI: Derivatives of 6-Piperazinobenzo[b]-Pyridol[3,2-f]Thiepin | Collection Czech. Chem. Community (Vol. 38), pp. 1693–1699 (1973) |
| 18. | Casey, D. E. | Extrapyramidal Syndromes | CMS Drugs, 5 Supp., pp. 1–12 (1996) (Casey 1996) |
| 19. | Farde, L., et al. | Positron Emission Tomographic Analysis of Central $D_1$ and $D_2$ Dopamine Receptor Occupancy in Patients Treated With Classical Neuroleptics and Clozapine | Arch. Gen. Psychiatry, Vol. 49, pp. 538–544 (1992) (Farde et al. 1997) |
| 20. | Farde, L., et al. | Central D2-Dopamine Receptor Occupancy in Schizophrenic Patients Treated with Antipsychotic Drugs | Arch. Gen. Psychiatry, Vol. 45, pp. 71–76 (1988) (Farde et al. 1997) |
| 21. | Jegouzo, A., et al. | Comparative oxidation of loxapine and clozapine by human neutrophils | Fundam. Clin. Pharmacol. Vol. 13, pp. 113–119 (1999) (Jegouzo et al. 1999) |
| 22. | Jiler, J., et al. | Neurotrope Und Psychotrope Substanzen. XIX: 8-Halogenderivate von 10-(4-Methylpiperazino)-10,11-Dihydrodibenzo(b,f)-Thiepin und Verwandte Substanzen | Collection Czech. Chem. Community (Vol. 33), pp. 1831–1845 (1968) |
| 23. | Kapur, S., et al. | Does Fast Dissociation From the Dopamine $D_2$ Receptor Explain the Action of Atypical Antipsychotics?: A New Hypothesis | Am. J. Psychiatry, Vol. 158: 3, pp. 360–369 (March 2001) |
| 24. | Kapur, S., et al. | Antipsychotic agents differ in how fast they come of the dopamine $D_2$ receptors. Implications for atypical antipsychotic action | J. Psych. & Neuroscience, Vol. 25, No. 2, pp. 161–166 (2000) (Kapur and Seeman 2000a) |
| 25. | Kapur, S., et al. | Are Animal Studies of Antipsychotics Appropriately Dosed?: Lessons From the Bedside to the Bench | Can. J. Psychiatry, Vol. 45, pp. 241–245 (2000) (Kapur et al. 2000b) |
| 26. | Liegeois, J. F., et al. | Pyrodibenzoxazepine and Pyridobenzothiazepine Derivatives as Potential Central Nervous System Agents: Synthesis and Neurochemical Study | J. Med. Chem. Vol. 37, pp. 519–525, 1994 |
| 27. | Moore, K. | Interactions between Prolactin and Dopaminergic Neurons | Biology of Reproduction, Vol. 36, pp. 47–58 (1987) (Moore 1987) |
| 28. | Pelz, K., et al. | Neurotrope und Psychotrope Substanzen. XXV: Uber die in 8- Stellung Durch die Methyl-, Tert- Butyl-, Methoxy-, Methylthio-, und methansulfonylgruppe Substituierten 10-(4-Methylpiperazino)-10,11-Dihydro-dibenzo[b,f]Thiepin-Derivate | Collection Czech. Chem. Community (Vol. 33), pp. 1895–1910 (1968) |
| 29. | Robertson, G. et al. | Induction Patterns of Fos-Like Immunoreactivity in the Forebrain as Predictors of Atypical Antipsychotic Activity | Jnl. Pharmacol. & Exper. Therap. Vol. 271, No. 2, pp. 1058–1066, 1994 (Robertson et al. 1994) |
| 30. | Seeman, P. et al. | Deriving the therapeutic concentrations for clozapine and haloperidol: The apparent dissociation constant of a neuroleptic at the dopamine $D_2$ receptor varies with the affinity of the competing radioligand | Eur. Jnl of Pharmac., Molecular Pharmac. Section 291, pp. 59–66, (1993) (Seeman 1993) |
| 31. | Seeman, P. et al. | Antipsychotic drugs which elicit little or no Parkinsonism bind more loosely than dopamine to brain D2 receptors, yet occupy high levels of these receptors | Molecular Psych. Vol. 3, pp. 123–134, (1998) (Seeman and Tallerico 1998) |
| 32. | Seeman, P. et al. | Rapid release of Antipsychotic Drugs From Dopamine $D_2$ Receptors: An Explanation for Low Receptor Occupancy and Early Clinical Relapse Upon Withdrawal of Clozapine or Quetiapine | Am. J. Psychiatry, Vol. 156, pp. 676–684 (1999) |
| 33. | Uetrecht, J. et al. | Structural features associated with reactive metabolite formation in clozapine analogues | Chemico-Biological Interactions, Vol. 104, pp. 117–129 (1997) (Uetrecht et al. 1997) |
| 34. | Uetrecht, J. et al. | Reactive metabolites and agranulocytosis | Eur. Jnl Haemotology, Vol. 57, pp. 83–88 (1996) (Uetrecht 1996) |
| 35. | Wadenberg, M. et al. | Dopamine $D_2$ receptor occupancy predicts catalepsy and the suppression of conditioned avoidance response behavior in rats | Psychopharmacology, Vol. 150, pp. 420–429 (2000) (Wadenberg M. L. et al. 2000) |

All publications, references, articles, patents and patent applications cited herein are herein incorporated by reference in their entirety to the same extent as if each individual publication, patent or patent application was specifically and individually indicated to be incorporated by reference in its entirety.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

What is claimed is:

1. A compound, or a pharmaceutically acceptable salt thereof, wherein said compound is selected from the group consisting of:

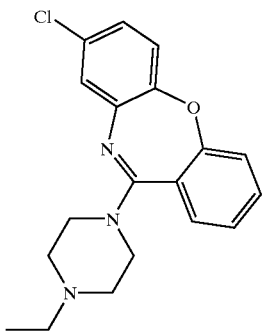

(A-6)=8-Chloro-11-(4-ethylpiperazin-1-yl)-dibenzo[b,f][1,4]oxazepine; and

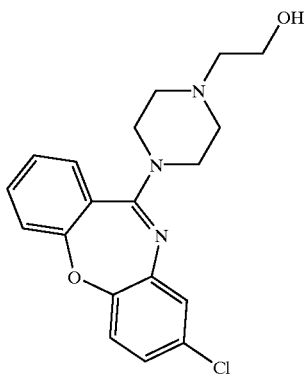

(A-7)=8-Chloro-11-(4-(2'-hydroxyethyl)piperazin-1-yl)-dibenzo[b,f][1,4]oxazepine.

2. A compound of Formula (A-6) or a pharmaceutically acceptable salt thereof, wherein said Formula (A-6) is represented by:

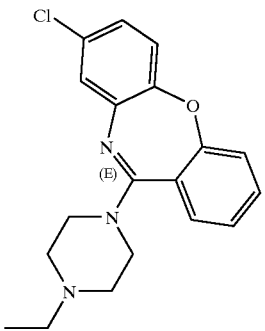

(A-6)=8-Chloro-11-(4-ethylpiperazin-1-yl)-dibenzo[b,f][1,4]oxazepine.

3. A compound of Formula (A-7) or a pharmaceutically acceptable salt thereof, wherein said Formula (A-7) is represented by:

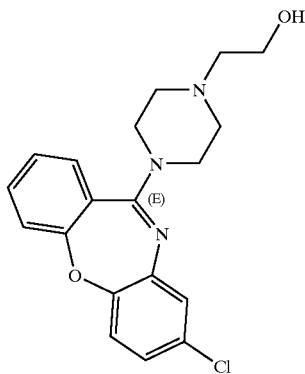

(A-7)=8-Chloro-11-(4-(2'-hydroxyethyl)piperazin-1-yl)-dibenzo[b,f][1,4]oxazepine.

4. A compound of Formula (A-13) or a pharmaceutically acceptable salt thereof, wherein said Formula (A-13) is represented by:

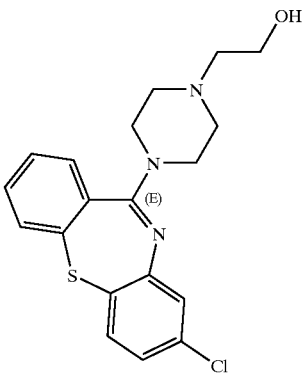

(A-13)=8-Chloro-11-(4-(2'-hydroxyethyl)piperazin-1-yl)-dibenzo[b,f][1,4]thiazepine.

5. A method for the treatment of psychosis, said method comprising the step of administering a therapeutically effective amount of a compound of Formula (A-6) or a pharmaceutically acceptable salt thereof, wherein said Formula (A-6) is represented by:

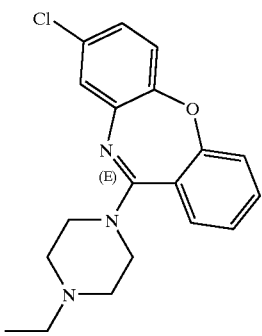

(A-6)=8-Chloro-11-(4-ethylpiperazin-1-yl)-dibenzo[b,f][1,4]oxazepine.

6. A method for the treatment of psychosis, said method comprising the step of administering a therapeutically effective amount of a compound of Formula (A-7) or a pharmaceutically acceptable salt thereof, wherein said Formula (A-7) is represented by:

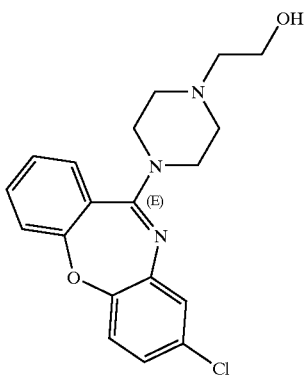

(A-7)=8-Chloro-11-(4-(2'-hydroxyethyl)piperazin-1-yl)-dibenzo[b,f][1,4]oxazepine.

7. A method for the treatment of psychosis, said method comprising the step of administering a therapeutically effective amount of a compound of Formula (A-13) or a pharmaceutically acceptable salt thereof, wherein said Formula (A-13) is represented by:

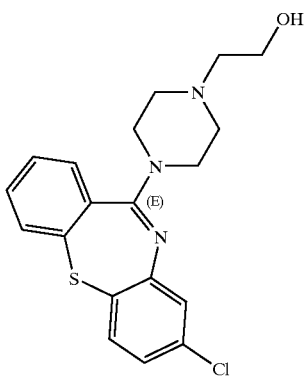

(A-13)=8-Chloro-11-(4-(2'-hydroxyethyl)piperazin-1-yl)-dibenzo[b,f][1,4]thiazepine.

8. A pharmaceutical composition comprising a compound of Formula (A-6) or a pharmaceutically acceptable salt thereof, and a pharmaceutically acceptable carrier, wherein said Formula (A-6) is represented by:

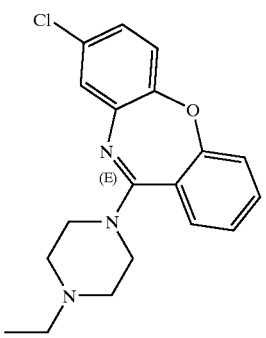

(A-6)=8-Chloro-11-(4-ethylpiperazin-1-yl)-dibenzo[b,f][1,4]oxazepine.

9. A pharmaceutical composition comprising a compound of Formula (A-7) or a pharmaceutically acceptable salt thereof, and a pharmaceutically acceptable carrier, wherein said Formula (A-7) is represented by:

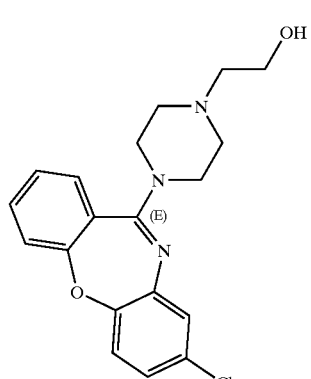

(A-7)=8-Chloro-11-(4-(2'-hydroxyethyl)piperazin-1-yl)-dibenzo[b,f][1,4]oxazepine.

10. A pharmaceutical composition comprising a compound of Formula (A-13) or a pharmaceutically acceptable salt thereof, and a pharmaceutically acceptable carrier, wherein said Formula (A-13) is represented by:

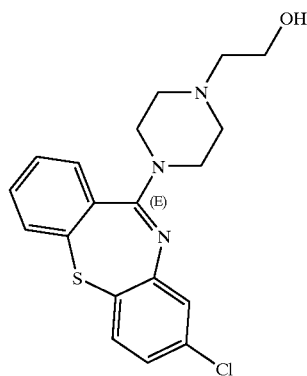

(A-13)=8-Chloro-11-(4-(2'-hydroxyethyl)piperazin-1-yl)-dibenzo[b,f][1,4]thiazepine.

* * * * *